United States Patent
Bohlen et al.

(10) Patent No.: US 9,945,840 B2
(45) Date of Patent: *Apr. 17, 2018

(54) NON-INVASIVE, IN VITRO FUNCTIONAL TISSUE ASSAY SYSTEMS

(75) Inventors: Heribert Bohlen, Köln (DE); Eugen Kolossov, Köln (DE); Ralf Kettenhofen, Bonn (DE); Melanie Scholz, Marburg (DE); Leo Fink, Köln (DE)

(73) Assignee: AXIOGENESIS AG, Cologne (DE)

( * ) Notice: Subject to any disclaimer, the term of this patent is extended or adjusted under 35 U.S.C. 154(b) by 2117 days.

This patent is subject to a terminal disclaimer.

(21) Appl. No.: 11/547,871

(22) PCT Filed: Apr. 7, 2005

(86) PCT No.: PCT/EP2005/003662
§ 371 (c)(1),
(2), (4) Date: Sep. 28, 2007

(87) PCT Pub. No.: WO2005/098425
PCT Pub. Date: Oct. 20, 2005

(65) Prior Publication Data
US 2008/0132422 A1    Jun. 5, 2008

(30) Foreign Application Priority Data
Apr. 7, 2004   (EP) .................... 04008497

(51) Int. Cl.
*G01N 33/50* (2006.01)
*G01N 33/543* (2006.01)

(52) U.S. Cl.
CPC ..... *G01N 33/5008* (2013.01); *G01N 33/5014* (2013.01); *G01N 33/5023* (2013.01); *G01N 33/5058* (2013.01); *G01N 33/5073* (2013.01); *G01N 33/5088* (2013.01); *G01N 33/5438* (2013.01); *G01N 2800/52* (2013.01)

(58) Field of Classification Search
CPC .................................................. C12Q 1/005
USPC ........................................................ 435/6.13
See application file for complete search history.

(56) References Cited

U.S. PATENT DOCUMENTS

| | | | |
|---|---|---|---|
| 4,937,190 A | 6/1990 | Palmenberg | |
| 5,464,764 A | 11/1995 | Capecchi | |
| 5,733,727 A | 3/1998 | Field | |
| 5,900,361 A | 5/1999 | Klebe et al. | |
| 5,928,943 A | 7/1999 | Franz | |
| 6,015,671 A | 1/2000 | Field | |
| 6,072,402 A | 6/2000 | Kniffin | |
| 6,080,576 A | 6/2000 | Zambrowicz | |
| 6,399,300 B1 | 6/2002 | Field | |
| 6,458,589 B1 | 10/2002 | Rambhatla et al. | |
| RE37,978 E | 2/2003 | Field | |
| 6,581,161 B1 | 6/2003 | Byford | |
| 6,602,711 B1 | 8/2003 | Thomson | |
| 6,632,628 B1 | 10/2003 | Olson et al. | |
| 6,657,104 B1 | 12/2003 | Grant et al. | |
| 6,844,184 B2 | 1/2005 | Kim et al. | |
| 7,045,353 B2 | 5/2006 | Benvenisty | |
| 7,105,344 B2 | 9/2006 | Hescheler | |
| 7,449,306 B2 | 11/2008 | Elson et al. | |
| 7,452,718 B2 | 11/2008 | Gold et al. | |
| 8,148,152 B2 | 4/2012 | Kolossov et al. | |
| 8,318,488 B1 | 11/2012 | Bohlen et al. | |
| 9,321,997 B2 | 4/2016 | Kolossov et al. | |
| 2002/0022268 A1 | 2/2002 | Xu et al. | |
| 2002/0072117 A1 | 6/2002 | Xu et al. | |
| 2002/0092035 A1 | 7/2002 | Hescheler | |
| 2002/0146678 A1 | 10/2002 | Benvenisty | |
| 2002/0160511 A1 | 10/2002 | Rambhatla et al. | |
| 2003/0022367 A1 | 1/2003 | Xu | |
| 2003/0027331 A1 | 2/2003 | Yan et al. | |
| 2003/0102958 A1 | 6/2003 | Gudmundsson | |
| 2003/0108895 A1 | 6/2003 | Field | |
| 2003/0119107 A1 | 6/2003 | Dang | |
| 2003/0170890 A1 | 9/2003 | Roenicke | |
| 2004/0003424 A1 | 1/2004 | Olson et al. | |
| 2004/0096432 A1 | 5/2004 | Fleischmann et al. | |
| 2004/0117196 A1 | 6/2004 | Brockman | |
| 2005/0165612 A1 | 7/2005 | Van Rysselberghe | |
| 2006/0168665 A1 | 7/2006 | Hescheler | |
| 2007/0014772 A1 | 1/2007 | Cohen et al. | |
| 2007/0258948 A1 | 11/2007 | Kolossov et al. | |
| 2008/0019952 A1 | 1/2008 | Kolossov et al. | |
| 2009/0328243 A1 | 12/2009 | Ehlich | |
| 2013/0102497 A1 | 4/2013 | Bohlen et al. | |
| 2016/0209398 A1 | 7/2016 | Bohlen et al. | |
| 2016/0209399 A1 | 7/2016 | Bohlen et al. | |
| 2016/0209400 A1 | 7/2016 | Bohlen et al. | |
| 2017/0160259 A1 | 6/2017 | Kolossov et al. | |

FOREIGN PATENT DOCUMENTS

| | | |
|---|---|---|
| DE | 299 439 | 5/1990 |
| DE | 19727962 | 7/1997 |
| DE | 198 43 234 | 3/2000 |
| DE | 199 62154.3 | 7/2001 |
| EP | 1297851 | 4/2003 |

(Continued)

OTHER PUBLICATIONS

Igelmund et al. (1999) Action potential propagation failures in long-term recordings from embryonic stem cell-derived cardiomyocytes in tissue culture. Pflugers Arch. 437: 669-679.*
Gonzalez et al. (1999, DDT, vol. 4(9), pp. 431-439).*
Wegener et al. (2000, Exp. Cell Res., vol. 259, pp. 158-166).*
Bork et al. (2015, Molecules, vol. 20, pp. 1003-1013).*
Igelmund et al. (1999, Eur. J. Physiol., vol. 437, pp. 669-679).*

(Continued)

*Primary Examiner* — Thaian N Ton
*Assistant Examiner* — David A Montanari
(74) *Attorney, Agent, or Firm* — Seyfarth Shaw LLP

(57) ABSTRACT

Provided are functional cell and tissue assay systems based on substrate-integrated multifunctional microelectrode arrays implementing stem cell technology. The system covers normal and pathogenic characteristics.

12 Claims, 1 Drawing Sheet

(56) References Cited

FOREIGN PATENT DOCUMENTS

| | | |
|---|---|---|
| EP | 1348019 | 10/2003 |
| EP | 1970446 | 9/2008 |
| GB | 2 342 005 | 3/2000 |
| GB | 2 386 606 | 9/2003 |
| GB | 2 386 609 | 9/2003 |
| GB | 2 387 501 | 10/2003 |
| JP | 10292688 | 11/1998 |
| JP | 11-502702 | 3/1999 |
| JP | 2001-514883 | 9/2001 |
| JP | 2001-523106 | 11/2001 |
| JP | 2002-051782 | 2/2002 |
| JP | 2002-508670 | 3/2002 |
| JP | 2002-541832 | 12/2002 |
| JP | 2004-500065 | 1/2004 |
| JP | 2008-532474 | 8/2008 |
| JP | 2009-513107 | 4/2009 |
| JP | 2001-520170 | 10/2011 |
| WO | WO 1994/024274 | 10/1994 |
| WO | WO 1995/007463 | 3/1995 |
| WO | WO 1995/014079 | 5/1995 |
| WO | WO 1995/021191 | 8/1995 |
| WO | WO 1996/016163 | 5/1996 |
| WO | WO 1996/027675 | 9/1996 |
| WO | WO 1996/029395 | 9/1996 |
| WO | WO 1998/036081 | 8/1998 |
| WO | WO 98/49333 | 11/1998 |
| WO | WO 98/54294 * | 12/1998 |
| WO | WO 1999/001552 | 1/1999 |
| WO | WO 99/09152 | 2/1999 |
| WO | WO 1999/019471 | 4/1999 |
| WO | WO 00/63221 | 10/2000 |
| WO | WO 2001/062899 | 8/2001 |
| WO | WO 02/051987 A1 | 7/2002 |
| WO | WO 2002/074925 | 9/2002 |
| WO | WO 2002/097128 | 12/2002 |
| WO | WO 2003/006950 | 1/2003 |
| WO | WO 2003/010303 | 2/2003 |
| WO | WO 2003/016860 | 2/2003 |
| WO | WO 03/018760 A2 | 3/2003 |
| WO | WO 2003/046141 | 6/2003 |
| WO | WO 2003/080816 | 10/2003 |
| WO | WO 2004/011603 A2 | 2/2004 |
| WO | WO 2004/113515 A2 | 12/2004 |
| WO | WO 2005/005621 A2 | 1/2005 |
| WO | WO 2005/005662 A2 | 1/2005 |

OTHER PUBLICATIONS

Bremer, S., et al., "Establishment of an Embryotoxicity Assay with Green Fluorescence Protein-expressing Embryonic Cell-derived Cardiomyocytes", *Altern. Lab. Anim.* 27:471-484, Fund for the Replacement of Animals in Medical Experiments (1999).

Hescheler, J., et al., "Determination of Electrical Properties of ES Cell-derived Cardiomyocytes Using MEAs", *J. Electrocardiol.* 37:110-116 (Oct. 2004).

Igelmund, P., et al., "Action potential propagation failures in long-term recordings from embryonic stem cell-derived cardiomyocytes in tissue culture", *Pflügers Archiv—Eur. J. Physiol.* 437:669-679, Springer-Verlag (1999).

Ignatius, M.J., et al., "Bioactive surface coatings for nanoscale instruments: Effects on CNS neurons", *J. Biomed. Mater. Res.* 40:264-274, John Wiley & Sons (1998).

Kolossov, E., et al., "Functional Characteristics of ES Cell-derived Cardiac Precursor Cells Identified by Tissue-specific Expression of the Green Fluorescent Protein", *J. Cell Biol.* 143:2045-2056, The Rockefeller University Press (1998).

Kolossov, E., et al., "Identification and characterization of embryonic stem cell-derived pacemaker and atrial cardiomyocytes", *FASEB J.* 19:577-579, The Federation of American Societies for Experimental Biology (Apr. 2005).

Mummery, C., et al., "Differentiation of Human Embryonic Stem Cells to Cardiomyocytes: Role of Coculture With Visceral Endoderm-Like Cells", *Circulation* 107:2733-2740, American Heart Association (Jun. 2003).

Spielmann, H., et al., The use of transgenic embryonic stem (ES) cells and molecular markers of differentiation for improving the embryonic stem cell test (EST), *Congeni. Anom. (Kyoto)* 40:S8-S18, Japanese Teratology Society (2000).

International Search Report for International Application No. PCT/EP2005/003662, mailed on Jul. 15, 2005, European Patent Office, Rijswijk, NL.

U.S. Appl. No. 11/596,262, U.S. National Phase of PCT/EP05/05087, Int'l Filing Date May 11, 2005, § 371 Date Aug. 29, 2007, Not Yet Published.

U.S. Appl. No. 10/594,177, U.S. National Phase of PCT/EP04/07529, Int'l Filing Date Jul. 8, 2004, Not Yet Published.

International Preliminary Report on Patentability for International Application No. PCT/EP2005/003662, mailed on Mar. 17, 2006, European Patent Office, Munich, Germany.

English translation of JP 2002-051782.

JP Office Action for JP Appl. No. 2011-18577.

English translation of the JP Office Action, JP Appl. No. 2011-18577.

Llopis, Juan, et al.: "Measurement of cytosolic, mitochondrial, and Golgi pH in single living cells with green fluorescent proteins", Proc. Natl. Acad. Sci. USA, vol. 95, pp. 6803-6808, Jun. 1998.

Miesenöck, Gero, et al.: "Visualizing secretion and synaptic transmission with pH-sensitive green fluorescent proteins", Nature, vol. 394, pp. 192-195, Jul. 1998.

Miyawaki, Atsushi, et al.: "Fluorescent indicators for $Ca^{2+}$ based on green fluorescent proteins and calmodulin", Nature, vol. 388, pp. 882-887, Aug. 1997.

Amin and Pearce, "Glutamate toxicity in neuron-enriched and neuron-astrocyte co-cultures: effect of the glutamate uptake inhibitor L-trans-pyrrolidine-2,4-dicarboxylate," Neurocehm Int., 30(3):271-276 (1997).

Bush, et al., "A small molecular activator of cardiac hypertrophy uncovered in a chemical screen for modifiers of the calcineurin signaling pathway," PNAS, 101(9):2870-2875 (2004).

CA Application No. 2,525,847 Office Action dated Mar. 20, 2017.

CA Application No. 2,565,858 Amendment and Respnse filed Mar. 30, 2017.

Chung, et al., "Genetic engineering of mouse embryonic stem cells by Nurr1 enhances differentiation and maturation into dopaminergic neurons," Eur J Neurosci., 16(10):1829-1838 (2002).

Coppo, et al., "Constitutive and specific activation of STAT3 by BCR-ABL in embryonic stem cells," Oncogene, 22:4102-4110 (2003).

EP Application No. 04737076.2 Response filed Feb. 4, 2015.

EP Application No. 04737076.2 Response filed Nov. 11, 2014.

EP Application No. 04737076.2 Summons dated Jun. 18, 2014.

EP Application No. 05730775.5 Response filed Feb. 24, 2017.

EP Application No. 16165848.9 Communication dated Sep. 26, 2016.

EP Application No. 16165848.9 Response filed Mar. 16, 2017.

Rolletschek, et al., "Embryonic stem cell-derived cardiac, neuronal and pancreatic cells as model systems to study toxicological effects," Toxicology Letters, 149:361-369 (2004).

Synowitz, et al., "GABAA-receptor expression in glioma cells is triggered by contact with neuronal cells," European Journal of Neuroscience, 14:1294-1302 (2001).

U.S. Appl. No. 15/047,506 Non-Final Office Action dated Jun. 7, 2016.

Wobus, et al., "Pluripotent mouse embryonic stem cells are able to differentiate into cardiomyocytes expressing chronotropic responses to adrenergic and cholinergic agents and $CA^{2+}$ channel blockers," Differentiation, 48:173-182 (1991).

Zandstra, et al., "Scalable Production of Embryonic Stem Cell-Derived Cardiomyocytes," Tissue Engineering, 9(4):767-778 (2003).

Zwaka and Thomson, "Homologous recombination in human embryonic stem cells," Nature Biotechnology, 21: 319-321 (2003).

"1998 Information for Contributors," Science 279:108 (1998).

(56) References Cited

OTHER PUBLICATIONS

"Burning Bridges," Nat Biotechnol. 25(1):2 (2007).
"Common position (EC) No. 19/98," Official Journal of the European Communities, pp. C110/17-C110/34, Apr. 8, 1998.
"people: James Thomson—A transplant medicine revolutionary", The Business Journal 17(31):43 (2000).
Abeyta, et al., "Unique gene expression signatures of independently-derived human embryonic stem cell lines," Human Molecular Genetics 13(6):601-608 (2004).
Abuljadayel Is, "Induction of stem cell-like plasticity in mononuclear cells derived from unmobilised adult human peripheral blood," Curr Med Res Opin 19(5):355-75 (2003).
Alberts, et al., "Manipulating Proteins, DNA, and RNA", Molecular Biology of the Cell, fourth edition, Chapter 8, 2002, pp. 469-546.
Amit and Itskovitz-Eldor, "Derivation and spontaneous differentiation of human embryonic stem cells," J Anat 200(Pt 3):225-32 (2002).
Amit, M., et al., "Human Feeder Layers for Human Embryonic Stem Cells," Biology of Reproduction 68:2150-2156 (2003).
Annex to the communication opposition for European Application No. 05 740 642.3, dated Jun. 13, 2013, 8 pages.
Anson, et al., "Human induced pluripotent stem cell derived cardiomyocytes enable large scale robust assays of cardiac hypertrophy", www.cellulardynamics.com, 1 pages, (No Date Available), Cellular Dynamics International, Inc., Madison, WI USA and GlaxoSmithKline King of Prussia PA.
AU Application No. 2004256209 Office Action dated Jul. 8, 2009.
AU Application No. 2004256209 Statement of Proposed Amendments filed Mar. 11, 2010.
Banach et al., "Development of electrical activity in cardiac myocyte aggregates derived from mouse embryonic stem cells," Am J Physiol Heart Circ Physiol. 284(6):H2114-23 (2003).
Banai et al., "PDGF-Receptor Tyrosine Kinase Blocker AG1295 Selectively Attenuates Smooth Muscle Cell Growth In Vitro and Reduces Neointimal Fomration After Balloon Angioplasty in Swine," Circulation 97:1960-69 (1998).
Bauwens et al., "Development of a Perfusion Fed Bioreactor for Embryonic Stem Cell-Derived Cardiomyocyte Generation: Oxygen-Mediated Enhancement of Cardiomyocyte Output," Biotechnology and Bioengineering 90(4):452-61 (2005).
Boheler et al., "Differentiation of Pluripotent Embryonic Stem Cells into Cardiomyocytes," Circ. Res. 91(3):189-201 (2002).
Bongso, A., et al., "Isolation and culture of inner cell mass cells from human blastocysts," Human Reproduction 9:2110-2117 (1994).
Brevini et al., "No shortcuts to pig embryonic stem cells," Theriogeneology 74(4):544-50 (2010).
Buta et al., "Reconsidering pluripotency tests: do we still need teratoma assays?" Stem Cell Res. 11(1):552-62 (2013).
CA Application No. 2,525,847 Amendment and Response filed May 20, 2015.
CA Application No. 2,525,847 Amendment and Response filed May 22, 2014.
CA Application No. 2,525,847 Amendment and Response filed Sep. 29, 2011.
CA Application No. 2,525,847 Office Action dated Aug. 13, 2012.
CA Application No. 2,525,847 Office Action dated Feb. 16, 2016.
CA Application No. 2,525,847 Office Action dated Mar. 29, 2011.
CA Application No. 2,525,847 Office Action dated Nov. 20, 2014.
CA Application No. 2,525,847 Office Action dated Nov. 22, 2013.
CA Application No. 2,525,847 Response filed Aug. 16, 2016.
CA Application No. 2,558,946 Amendment and Response filed Nov. 8, 2012.
CA Application No. 2,558,946 Amendment and Response filed Sep. 1, 2011.
CA Application No. 2,558,946 Office Action dated Mar. 2, 2011.
CA Application No. 2,558,946 Office Action dated May 10, 2012.
CA Application No. 2,560,334 Amendment and Response filed Jul. 19, 2012.
CA Application No. 2,560,334 Office Action dated Jan. 19, 2012.
CA Application No. 2,560,334 Office Action dated Oct. 9, 2012.
CA Application No. 2,565,858 Amendment and Response filed Feb. 5, 2016.
CA Application No. 2,565,858 Amendment and Response filed Jun. 11, 2012.
CA Application No. 2,565,858 Amendment and Response filed Oct. 10, 2014.
CA Application No. 2,565,858 Amendment and Response filed Sep. 27, 2013.
CA Application No. 2,565,858 Office Action dated Apr. 10, 2014.
CA Application No. 2,565,858 Office Action dated Aug. 6, 2015.
CA Application No. 2,565,858 Office Action dated Dec. 13, 2011.
CA Application No. 2,565,858 Office Action dated Mar. 28, 2013.
CA Application No. 2,565,858 Office Action dated Sep. 20, 2016.
Carpenter et al., "Characterization and Differentiation of Human Embryonic Stem Cells," Cloning and Stem Cells 5(1):79-88 (2003).
Carvajal-Vergara, et al., "Patient-specific induced pluripotent stem-cell-derived models of Leopard syndrome," Nature, vol. 465, 808-814, Jun. 2010.
Cell Biology ATCC No. SCRC-2002 excerpt (Nov. 6, 2009).
Chalfont St. Giles, "GE Healthcare and Cellular Dynamics International Agree to Sublicense for Cellular Assay Patents", Dec. 18, 2012, 2 pages.
Chen, et al., "Differentiation trapping screen in live culture for genes expressed in cardiovascular lineages," Dev. Dyn., 229(2):319-27, Feb. 2004.
Chung, et al., "Human Embryonic Stem Cell Lines Generated without Embryo Destruction", Cell Stem Cell (2008) pp. 1-5.
Cowan et al., "Derivation of Embryonic Stem-Cell Lines from Human Blastocyts," The New England Journal of Medicine 350(13):1353-1356 (2004).
Dang et al., "Controlled, Scalable Embyronic Stem Cell Differentiation Culture," Stem Cells 22:275-282 (2004).
Dang et al., "Efficiency of Embryoid Body Formation and Hematopoietic Development from Embryonic Stem Cells in Different Culture Systems," Biotechnol Bioeng 78(4):422-453 (2002).
Davila et al., "Use and Application of Stem Cells in Toxicology," Toxicological Sciences 79:214-23 (2004).
Directive 98/44/EC of the European Parliament and of the Council, Official Journal of the European Communities, pp. L213/13-L213/21, Jul. 30, 1998.
Drab et al., "From totipotent embryonic stem cells to spontaneously contracting smooth muscle cells: a retinoic acid and db-cAMP in vitro differentiation model," Faseb J 11(11):905-15 (1997).
Enlarged Board of Appeal: "Decision G1/98," Official Journal EPO, pp. 111-141, Mar. 2000.
JP 10292688, Machine translated English copy; cited as Document C15.
WO 2002/097128, Machine translated English copy, cited as Document C30.
EP Application No. 04737076.2 Brief Communication dated Nov. 21, 2014.
EP Application No. 04737076.2 Communication dated Dec. 6, 2010.
EP Application No. 04737076.2 Communication dated Jun. 19, 2014.
EP Application No. 04737076.2 Communication dated Mar. 12, 2013.
EP Application No. 04737076.2 Communication dated Sep. 24, 2012.
EP Application No. 04737076.2 Invitation pursuant to Article 94(3) and Rule 71(1) EPC dated Dec. 10, 2014.
EP Application No. 04737076.2 Response filed Dec. 4, 2014.
EP Application No. 04737076.2 Response filed Jan. 16, 2013.
EP Application No. 04737076.2 Response filed Jul. 9, 2013.
EP Application No. 04737076.2 Response filed Mar. 22, 2011.
EP Application No. 04740822.4 Communication dated Apr. 26, 2006.
EP Application No. 04740822.4 Communication dated Jan. 22, 2008.
EP Application No. 04740822.4 Communication dated Jan. 23, 2013.

(56) References Cited

OTHER PUBLICATIONS

EP Application No. 04740822.4 Communication dated Jul. 21, 2009.
EP Application No. 04740822.4 Communication dated Jun. 10, 2008.
EP Application No. 04740822.4 Communication dated Nov. 24, 2010.
EP Application No. 04740822.4 Invitation dated Oct. 10, 2013.
EP Application No. 04740822.4 Response filed Jan. 9, 2014.
EP Application No. 04740822.4 Response filed Jun. 3, 2013.
EP Application No. 04740822.4 Response filed Mar. 16, 2011.
EP Application No. 04740822.4 Response filed May 20, 2008.
EP Application No. 04740822.4 Response filed Nov. 6, 2009.
EP Application No. 04740822.4 Response filed Oct. 16, 2008.
EP Application No. 05730755.5 Communication dated Jul. 8, 2011.
EP Application No. 05730755.5 Communication dated Oct. 21, 2016.
EP Application No. 05730775.5 Response filed Jan. 16, 2012.
EP Application No. 05740642.3 Communication dated Jan. 5, 2010.
EP Application No. 05740642.3 First Office Action dated Dec. 27, 2007.
EP Application No. 05740642.3 Invitation pursuant to Article 94(3) and Rule 71(1) EPC dated May 13, 2009.
EP Application No. 05740642.3 Minutes dated Dec. 9, 2013.
EP Application No. 05740642.3 Petition filed Dec. 9, 2009.
EP Application No. 05740642.3 Response filed Apr. 29, 2008.
EP Application No. 05740642.3 Response filed Jan. 28, 2010.
EP Application No. 05740642.3 Response filed Jul. 23, 2009.
EP Application No. 05740642.3 Response filed Mar. 30, 2012.
EP Application No. 05740642.3 Response filed Oct. 28, 2013.
EP Application No. 05740642.3 Response filed Sep. 26, 2013.
EP Application No. 10010425.6 Communication dated Aug. 25, 2014.
EP Application No. 10010425.6 Communication dated Mar. 7, 2011.
EP Application No. 10010425.6 Communication dated Oct. 19, 2012.
EP Application No. 10010425.6 European Search Report dated Feb. 2, 2011.
EP Application No. 10010425.6 Invitation pursuant to Article 94(3) and Rule 71(1) EPC dated Jul. 23, 2015.
EP Application No. 10010425.6 Response filed Apr. 29, 2013.
EP Application No. 10010425.6 Response filed Aug. 12, 2015.
EP Application No. 10010425.6 Response filed Sep. 1, 2011.
EP Application No. 10010425.6 Response filed Sep. 9, 2014.
EP Application No. 12197213.7 Communication dated Jun. 17, 2014.
EP Application No. 12197213.7 Communication dated Mar. 7, 2013.
EP Application No. 12197213.7 Communication dated Nov. 13, 2015.
EP Application No. 12197213.7 Extended European Search Result dated Mar. 8, 2013.
EP Application No. 12197213.7 Response filed Jan. 5, 2015.
EP Application No. 12197213.7 Response filed May 23, 2016.
EP Application No. 12197213.7 Response filed Oct. 10, 2013.
EP Application No. 16165848.9 European Search Report dated Jul. 14, 2016.
European Patent Office: "Notice of Opposition to European Patent No. 1745144," EP Patent Application No. 05740642.3, pp. 1-23, Aug. 19, 2011.
European Patent Office: Statement by the European Patent Office concerning the Resolution of the European Parliament of Oct. 4, 2001 on the patenting of BRCA1 and BRCA2 ("breast cancer") genes, pp. 1-5, Oct. 17, 2001.
Experimental Report: Stem Cells Derived Tissue Engineering in accordance with the teaching of WO 2004/113515.
Fassler, R., et al., "Differentiation and integrity of cardiac muscle cells are impaired in the absence of β1 integrin," J. Cell. Sci. 109:2989-2999, The Company of Biologists Limited, United Kingdom (1996).
Feld et al. "Electrophysiological Modulation of Cardiomyocytic Tissue by Transfected Fibroblasts Expressing Potassium Channels," Circulation 105:522-529, 2002.
Fijnvandraat, et al., "Cardiomyocytes derived from embryonic stem cells resemble cardiomyocytes of the embryonic heart tube," Cardiovascular Research 58:399-409 (2003).
Földes, et al., "Modulation of human embryonic stem cell-derived cardiomyocyte growth: A testbed for studying human cardiac hypertrophy?," Journal of Molecular Cardiology, 50, 367-376, 2011.
Fukuda, "Regeneration of cardiomyocytes from bone marrow: Use of mesenchymal stem cell for cardiovascular tissue engineering", Cytotechnology 41: 165-175, 2003.
Gepstein, L, "Derivation and Potential Applications of Human Embryonic Stem Cells," Circulation Research 91:866-876 (2002).
Glossary. In Stem Cell information. National Institutes of Health, U.S. Department of Health and Human Services, 2014.
Goldenthal, et al., "Stem cells and cardiac disorders: an appraisal", Cardiovascular Research 58 (2003) 369-377.
Gomez et al., "Derivation of cat embryonic stem-like cells from in vitro-produced blastocysts on homologous and heterologous feeder cells," Theriogeneology 74(4):498-515 (2010).
Guhr, et al., "Current state of human embryonic stem cell research: an overview of cell lines and their use in experimental work," Stem Cells 24(10):2187-91 (2006).
Gulbrandsen, Carl, Declaration dated Mar. 2, 2009.
Gumpel, M. et al., "Transplantation of Human Ebryonic Oligodendrocytes into Shiverer Brain," Annal New York Academy of Sciences 495:70-85 (1987).
Hakuno, et al., "Bone Marrow-Derived Regenerated Cardiomyocytes (CMG Cells) Express Functional Adrenergic and Muscarinic Receptors", Circulation, 2002, 105, pp. 380-386.
Haniel, "iPS Power," European Biopharmaceutical Review Winter 2013.
Harada et al., "Significance of Ventricular Myocytes and Nonmyocytes Interaction During Cardiocyte Hypertrophy," Circulation 96(10):3737-44 (1997).
Hattan, et al., "Purified cardiomyocytes from bone marrow mesenchymal stem cells produce stable intracardiac grafts in mice", Cardiovascular Research 65 (2005) 334-344.
He et al., "Human Embryonic Stem Cells Develop Into Multiple Types of Cardiac Myocytes: action potential characterization," Circ. Res. 93(1):32-9 (2003).
Heins, et al., "Derivation, Characterization, and Differentiation of Human Embryonic Stem Cells," Stem Cells 22:367-76 (2004).
Hescheler J., et al., "Embryonic stem cells: a model to study structural and functional properties in cardiomyogenesis," Cardiovascular Research 36:149-162, Elsevier Science (1997).
Hidaka, K, et al., "Chamber-specific differentiation of Nkx2.5-positive cardiac precursor cells from murine embryonic stem cells," FASEB J. 17:740-742, (2003).
Hoffman and Carpenter, "Characterization and culture of human embryonic stem cells," Nature Biotechnology 23(6):699-708 (2005).
Hovatta et al., "A culture system using human foreskin fibroblasts as feeder cells allows production of human embryonic stem cells," Human Reproduction 18(7):1404-09 (2003).
Hu et al., "Protective actions of salvianolic acid A on hepatocyte injured by peroxidation in vitro," World J Gastroentero 6(3):402-4004 (2000).
Huang, W-Y., et al., "Transgenic expression of green fluorescence protein can cause dilated cardiomyopathy," Nat. Med. 6:482-484, Nature American Inc. (May 2000).
iCell® Cardiomyocytes Application Protocol, "Modeling Cardiac Hypertrophy: Endothelin-1 Induction with qRT-PCR Analysis" Cellular Dynamics International, Feb. 2013, 7 pages.
International Application No. PCT/EP2004/006698, International Search Report dated Feb. 1, 2005.
International Application No. PCT/EP2004/007530 International Search Report dated Jan. 19, 2005.

(56) References Cited

OTHER PUBLICATIONS

International Application No. PCT/EP2005/005087, International Preliminary Report on Patentability dated Apr. 18, 2006.
International Application No. PCT/EP2005/005087, International Search Report dated Jan. 8, 2005.
International Society for Stem Cell Research, "Human ES Cell (hESC) Lines," (Jan. 21, 2010) http://www.isscr.org/science/sclines.htm.
Itskovitz-Eldor et al. "Differentiation of Huan Embryonic Stem Cells into Embryoid Bodies Comprising the Three Embryonic Germ Layers," Molecular Medicine 6(2):88-95, 2000.
Jean et al., "Pluripotent genes in avian stem cells," Dev Growth Differ. 55(1):41-51 (2013).
Jiang, Y. et al., "Pluripotency of Mesenchymal Stem Cells Derived from Adult Marrow," Nature 418:41-49 (2002).
Jones, et al., "Human iPSC-Derived Cardiomyocytes Provide a Relevant Model of Cardiac Hypertrophy for Phenotypic Screening and Drug Discovery", www.cellulardynamics.com, 1 page, (No Date Available), Cellular Dynamics International, Inc., Madison, WI USA and Molecular Devices, Sunnyvale, CA.
JP Application No. 2006-516014 Office Action dated May 13, 2011.
JP Application No. 2006-516014 Office Action dated May 18, 2010.
JP Application No. 2006-516014 Response filed Jul. 22, 2010.
JP Application No. 2006-516014 Response filed May 13, 2011.
JP Application No. 2006-518153 Decision of Refusal dated Mar. 17, 2011.
JP Application No. 2006-518153 Notice of Appeal and Brief filed Jul. 1, 2011.
JP Application No. 2006-518153 Notification of Reasons for Refusal dated Feb. 27, 2009.
JP Application No. 2006-518153 Notification of Reasons for Refusal dated Mar. 16, 2010.
JP Application No. 2006-518153 Response filed May 16, 2010.
JP Application No. 2006-518153 Response filed May 27, 2009.
JP Application No. 2007-506726 Office Action dated Dec. 7, 2010.
JP Application No. 2007-506726 Office Action dated Jul. 10, 2012.
JP Application No. 2007-506726 Office Action dated Nov. 24, 2011.
JP Application No. 2007-506726 Response filed Feb. 9, 2012.
JP Application No. 2007-506726 Response filed Mar. 21, 2011.
JP Application No. 2007-512085 Notification of Reasons for Refusal dated Dec. 3, 2010.
JP Application No. 2007-512085 Notification of Reasons for Refusal dated May 13, 2011.
JP Application No. 2007-512085 Response filed Feb. 18, 2011.
JP Application No. 2007-512085 Response filed Jul. 18, 2011.
JP Application No. 2011-14701 Inquiry dated Feb. 14, 2013.
JP Application No. 2011-14701 Notification of Reasons for Refusal dated Aug. 22, 2013.
JP Application No. 2011-157310 Decision of Refusal dated Aug. 1, 2013.
JP Application No. 2011-157310 Notice of Appeal and Brief filed Nov. 27, 2013.
JP Application No. 2011-157310 Notification of Reasons for Refusal dated Jan. 15, 2013.
JP Application No. 2011-157310 Response filed Jan. 17, 2015.
JP Application No. 2011-157310 Response filed Sep. 5, 2014.
JP Application No. 2011-157310 Response filed Sep. 9, 2015.
JP Application No. 2013-23188 Appeal Decision dated Nov. 9, 2015.
JP Application No. 2013-23188 Inquiry dated Jun. 23, 2014.
JP Application No. 2013-23188 Notification of Reasons for Refusal dated Mar. 10, 2015.
Kehat, I., et al., "Human embryonic stem cells can differentiate into mycytes with structural and functional properties of cardiomyocytes," J. Clin. Invest. 108:407-414, (2001).
Kettenhofen, R., et al., "Transgenic Murine Embryonic Stem Cells as an in vitro Model for Developmental Toxicity—An Alternative to the Gold Standard," Naunyn-Schmiedeberg's Arch. Pharmacol 365, Suppl. 1:R154, Springer Verlag, Abstract No. 601 (Mar. 2002).
Kikuchi, K., et al., "Roles of Embryonic Astrocytes and Schwann Cells in Regeneration of Adult Rat Dorsal Root Axons: Qualitative Observations," Neurol. Med. Chir. 33: 682-690 (1993).
Kim et al., "Pluripotent stem cells induced from adult neural stem cells by reprogramming with two factors," Nature 454:646-650 (2008).
Klimanskaya, I., et al., "Human Embryonic Stem Cell Lines Derived from Single Blastomere," Nature 444: 1-5 (2006).
Klug et al., "Genetically Selected Cardiomyocytes from Differentiating Embryonic Stem Cells Form Stable Intracardiac Grafts," J. Clin. Invest. 98(1):216-24 (1996).
Kolossov, E., et al., "Transplantation of the Cardiomyocytes Selected from Transgenically Designed ES cells: Quality Control and Engrafting Support of Fibroblasts," Tissue Engineering 9:853-854, Mary Ann Liebert, Inc., Abstract No. 230 (Aug. 2003).
Kulkarni and Khanna, "Functional hepatocyte-like cells derived from mouse embryonic stem cells: A novel in vitro hepatotoxicity model for drug screening," Toxicology in Vitro 20:1014-22 (2006).
Kurosawa, Hiroshi "Methods for Inducing Embryoid Body Formation: In Vitro Differentiation System of Embryonic Stem Cells," J. Bioscience and Bioengineering 103(5):389-98 (2007).
Lavon and Benvensity, "Differentiation and Genetic Manipulation of Human Embryonic Stem Cells and the Analysis of the Cardiovascular System," Trends in Cardiovascular Medicine 13(2):47-52 (2003).
Makino, et al., "Cardiomyocytes can be generated from marrow stromal cells in vitro", The Journal of Clinical Investigation, vol. 103, No. 5, Mar. 1999, pp. 697-706.
Maltsev, V.A., et al., "Cardiomyocytes Differentiated in Vitro From Embryonic Stem Cells Developmentally Express Cardiac-Specific Genes and Ionic Currents," Circulation Research 75:233-244, (1994).
Mandel et al. "The Electrophysiologic Effects of Low and High Digoxin Concentrations on Isolated Mammalian Cardiac Tissue: Reversal by Digoxin-Specific Antibody," Journal of Clinical Investigation 51:1378-1387, 1972.
Mann et al., "Human iPSC-Derived Hepatocystes," Genetic Engineering & Biotechnology News 33(9) (2013).
Matter, et al., "Abstract 15561: A Novel Functional Model of Cardiac Hypertrophy Using Human Induced Pluripotent Stem Cell-Derived Cardiomyocytes", Circulation, 2011; 124 (10021) A15561, 2 pages.
Meyer, N., et al., "A fluorescent reporter gene as a marker for ventricular specification in ES-derived cardiac cells," FEBS Lett. 478:151-158, (2000).
Miller and Bloom, "Publishing Controversial Research," Science 282:104 (1998).
Miller-Hance et al., "In Vitro Chamber Specification during Embryonic Stem Cell Cardiogenesis," The Journal of Biological Chemistry 268(33):25244-25252 (1993).
Mitalipova et al., "Human embryonic stem cell lines derived from discarded embryos," Stem Cells 21(5):521-6 (2003).
Molkentin, et al., "A Calcineurin-Dependent Transcriptional Pathway for Cardiac Hypertrophy," Cell, vol. 93, Apr. 17, 1998, pp. 215-228.
Montgomery et al., "Activation of endothelial-leukocyte adhesion molecule 1 (ELAM-1) gene transcription," Proc. Natl. Acad. Sci. USA 88:6523-27 (1991).
Muller, M., et al., "Selection of ventricular-like cardiomyocytes from ES cells in vitro," FASEB J. 14:2540-2548, The Federation of American Societies for Experimental Biology (2000).
Munoz et al., "Conventional pluripotency markers are unspecific for bovine embryonic-derived cell-lines," Theriogeneology 69(9):1159-64 (2008).
Muthuchamy et al., "Developmental Analysis Tropomyosin Gene Expression in Embryonic Stem Cells Mouse Embryos," Molecular and Cellular Biology 13(6):3311-23 (1993).
National Institute of Health resoursce "Providers with at least One Cell Line Available for Shipping," (Jul. 1, 2010) http://stemcells.nih.gov/research/registry/available.asp.
National Stem Cell Bank, "Deposited Cell Lines," (Jul. 22, 2009) https://www.wicell.org/index.php?option=com_oscommerce&Itemid=192.

(56) References Cited

OTHER PUBLICATIONS

National Stem Cell Bank, "Deposited Cell Lines," (Nov. 6, 2009) https://www.wicell.org/index.org/index.php?option=com_oscommerce&Itemid=192.
Nguyen et al., "Methods to assess stem cell lineage, fate and function," Advanced Drug Delivery Reviews 62(12):1175-86 (2010).
NIH Human Embryonic Stem Cell registry, On-Line Publication, http://escr.ih.gov/, retrieved May 13, 2003.
NIH Stem Cell Guidelines, sections III-V, 11 total pages.
Opposition Division: "Interlocutory decision in Opposition proceedings of file 85 304 490.7," pp. 1-29, Jan. 16, 2003.
Opposition Division: "Interlocutory decision in Opposition proceedings of file 94 913 174.2," pp. 1-29, Jul. 21, 2003.
P. Simpson, "Stimulation of hypertrophy of cultured neonatal rat heart cells through an alpha 1-adrenergic receptor and induction of beating through an alpha 1- and beta 1-adrenergic receptor interaction. Evidence for independent regulation of growth and beating", Circ. Res., 1985, 56, pp. 884-894.
Paris and Stout, "Equine embryos and embryonic stem cells: defining reliable markers of pluripotency," Theriogeneology 74(4):516-24 (2010).
PRLog (Press Release), Jun. 12, 2013, Cologne, Germany, "iPS Academia Japan and Axiogenesis Expand Partnership", 2 pages, iPS Academia Japan and Axiogenesis Expand Partnership.
Rajabalian, S., et al., "Supportive Effects of Human Embryonic Fibroblast Cell Lines on Growth and Proliferation of EBV-Transformed Lymphoblastoid Cells," Iranian Biomedical Journal 7(4):147-153 (2003).
Reubinoff, et al., "Embryonic stem cell lines from human blastocysts: somatic differentiation in vitro," Nature Biotechnology 18:399-404 (2000).
Richards et al., "Human feeders support prolonged undifferentiated growth of human inner cell masses and embryonic stem cells," Nature Biotechnology 20:933-36 (2002).
Rohwedel et al., "Muscle cell differentiation of embryonic stem cells reflects myogenesis in vivo: developmentally regulated expression of myogenic determination genes and functional expression of ionic currents," Dev. Biol 164(1):87-101 (1994).
Sabbah, "Biologic Rationale for the Use of Beta-Blockers in the Treatment of Heart Failure," Heart Failure Reviews, 9, 91-97, 2004.
Sachinidis, A., et al., "Cardiac specific differentiation of mouse embryonic stem cells," Cardiovascular Research 58:278-291, May 2003.
Schlaeger et al., "Uniform vascular-endothelial-cell-cpecific gene expression in both embyonic and adult transgenic mice," Proc. Natl. Acad. Sci. USA 94:3058-63 (1997).
Schreckenberg, et al., "Inhibition of $Ca^{2+}$—dependent PKC isoforms unmasks ERK-dependent hypertrophic growth evoked by phenylephrine in adult ventricular cardiomyocytes", Cardiovascular Research, 63 (2004) pp. 553-560.
Schwengberg, Silke, Declaration dated Sep. 24, 2009 filed in U.S. Appl. No. 10/594,188.
Sei, et al., "The alpha-adrenergic stimulation of atrial natriuretic factor expression in cardiac myocytes requires calcium influx, protein kinase C, and calmodulin-regulated pathways," J. Biol. Chem., 266(24):15910-6, 1991.
Seiler et al., "Etablierung molekularer Endpunkte zur Weiterentwicklung des Embryonalen Stammzelltests (EST) mit embryonalen Stammzellen der Mans (Zeillinie D3)," ALTEX 19:55-63 (2002) (English Summary on p. 55).
Shamblott, M.J. et al., "Derivation of Pluripotent Stem Cells from Cultured Human Primordial Germ Cells," Proc. Natl. Acad. Sci. 95:13726-13731 (1998).
Submission Before Oral Proceedings for European Application No. 05 740 642.3, dated Nov. 6, 2013,10 pages.
Submission Before Oral Proceedings for European Application No. 05 740 642.3, dated Sep. 26, 2013, 13 pages.
Sugden, "Ras, Akt, and Mechanotransduction in the Cardiac Myocyte," National Heart and Lung Institute Division (Cardiac Medicine Section), Faculty of Medicine, Imperial College of Science, Technology and Medicine, London UK, Downloaded from circres.ahajournals.org on Oct. 28, 2010.
Suzuki, et al., "Endothelin stimulates hypertrophy and contractility of neonatal rat cardiac myocytes in a serum-free medium," FEBS Letters, vol. 268, No. 1, Jul. 1990, pp. 149-151.
Switzerland Federal Office of Public Health, "Human embyonic stem cells," (Jan. 7, 2010) https://www.bag.admin.ch/themen/medizin/03301/03304index.html?lang=en.
Takemura, et al., "Phenotype alteration of failing myocardium," Nippon Rinsho, 61(5):731-738, May 2003 (Abstract) Article in Japanese.
Technical Board of Appeal 3.3.4: "Decision T356/93-3.3.4", Official Journal EPO 8:545-585, Aug. 1995.
The National Institutes of Health, "Stem cell Information," datasheet from Technion-lsrael Institute of Technology, (Mar. 4, 2007), http://stemcells.nih.gov/research/registry/technion.asp.
The National Institutes of Health, "Stem cell Information," datasheet from University of California, San Francisco, (Feb. 19, 2007), http://stemcells.nih.gov/research/registry/ucsf.asp.
Thomson, et al., "Embryonic Stem Cell Lines Derived from Human Blastocysts," Science 282:1145-1147 (1998).
Torella et al., "Resident cardiac stem cells" Cell Mol Life Sci. 64:661-673 (2007).
U.S. Appl. No. 11/596,262 Final Office Action dated Jun. 17, 2010.
U.S. Appl. No. 11/596,262 Final Office Action dated Nov. 10, 2010.
U.S. Appl. No. 11/596,262 Non-Final Office Action dated Dec. 30, 2009.
U.S. Appl. No. 13/654,115 Non-Final Office Action dated Jul. 15, 2015.
U.S. Appl. No. 14/996,602 Non-Final Rejection dated Jan. 19, 2017.
U.S. Appl. No. 14/996,602 Response filed Apr. 19, 2017.
U.S. Appl. No. 14/996,622 Non-Final Rejection dated Jan. 17, 2017.
U.S. Appl. No. 14/996,622 Response filed Apr. 17, 2017.
U.S. Appl. No. 14/996,641 Advisory Action dated May 4, 2017.
U.S. Appl. No. 14/996,641 Final Office Action dated Nov. 10, 2016.
U.S. Appl. No. 14/996,641 Inverview Summary dated May 15, 2017.
U.S. Appl. No. 14/996,641 Non-Final Office Action dated Jun. 2, 2016.
U.S. Appl. No. 14/996,641 Response to Final Office Action filed Mar. 28, 2017.
U.S. Appl. No. 14/996,641 Response to Final Office Action filed May 10, 2017.
U.S. Appl. No. 14/996,641 Response to Non-Final Office Action filed Sep. 2, 2016.
University of Massachusetts Medical School, excerpts from International Stem Cell Registry, (Jan. 7, 2010).
Wartenberg et al., "The Embryoid Body as a Novel In Vitro Assay System for Antiangiogenic Agents," Lab Invest. 78(10):1301-14 (1998).
Wartenberg et al., "Tumor-induced angiogenesis studied in confrontation cultures of multicellular tumor spheroids and embryoid bodies grown from pluripotent embryonic stem cells," The FASEB Journal 15:995-1005 (2001).
Watanabe et al., "Stable production of mutant mice from double gene converted ES cells with puromycin and neomycin," Biochem Biophys Res Commun. vol. 213:130-137, 1995.
Weitzer G., et al., "Cytoskeletal Control of Myogenesis: A Desmin Null Mutation Blocks the Myogenic Pathway during Embryonic Stem Cell Differentiation," Dev. Biol. 172:422-439, Academic Press, Inc., United States (1995).
White, et al., "Cardiac physiology at the cellular level: use of cultured HL-1 cardiomyocytes for studies of cardiac muscle cell structure and function," Am J Physiol Heart Circ Physiol, 286: H823-H829, 2004.
WO 2005/108598 Experimental Report 1.
WO 2005/108598 Experimental Report 2.
Wobus, A., et al., "Retinoic Acid Accelerates Embryonic Stem Cell-Derived Cardiac Differentiation and Enhances Development of Ventricular Cardiomyocytes," J. Mol. Cell Cardiol. 29:1525-1539, Academic Press, Ltd., United States (1997).
Xu et al., "Characterization and Enrichment of Cardiomyocytes Derived from Human Embryonic Stem Cells," Circ. Res. 91:501-508 (2002).

(56) References Cited

OTHER PUBLICATIONS

Yamamoto, et al., "Differentiation of Embryonic Stem Cells into Hepatocytes: Biological Functions and Therapeutic Application," Hepatology 37(5):983-93 (2003).
Yamashita, et al., "Histone deacetylase inhibitor trichostatin A induces cell-cycle arrest/apoptosis and hepatocyte differentiation in human hepatoma cells," Int. J. Cancer, 103(5): 572-6, 2003.
Yamazaki, T., et al., "Molecular Mechanism of Cardiac Cellular Hypertrophy by Mechanical Street," J. Mol. Cell. Cardiol. 27:133-140 (1995) [Abstract #0536].
Yamda et al., "In Vitro Differentiation of Embryonic Stem Cells into Hepatocyte-Like Cells Identified by Cellular Uptake of Indocyanine Green," Stem Cells, 20:146-154, 2002.
Young, H.E. And Black, A.C., "Adult Stem Cells," The Anatomical Record Part A 276A: 75-102 (2004).
Zhao, Y. et al., "A Human Peripheral Blood Monocyte-Derived Subset Acts as Pluripotent Stem Cells," PNAS 100(5):2426-2431 (2003).
Zhou et al., "Humanized Murine Model for HBV and HCV Using Human Induced Pluripotent Stem Cells," Arch Pharm Res. 35(2):261-69 (2012).
Zweigerdt, et al., "Generation of confluent cardiomyocyte monolayers derived from embryonic stem cells in suspension: a cell source for new therapies and screening strategies," Cytotherapy 5(5):399-413, 2003.
DD 299 439, Machine translated English copy; cited as Document C4.
DE 198 43 234, Machine translated English copy; cited as Document C6.

\* cited by examiner

A
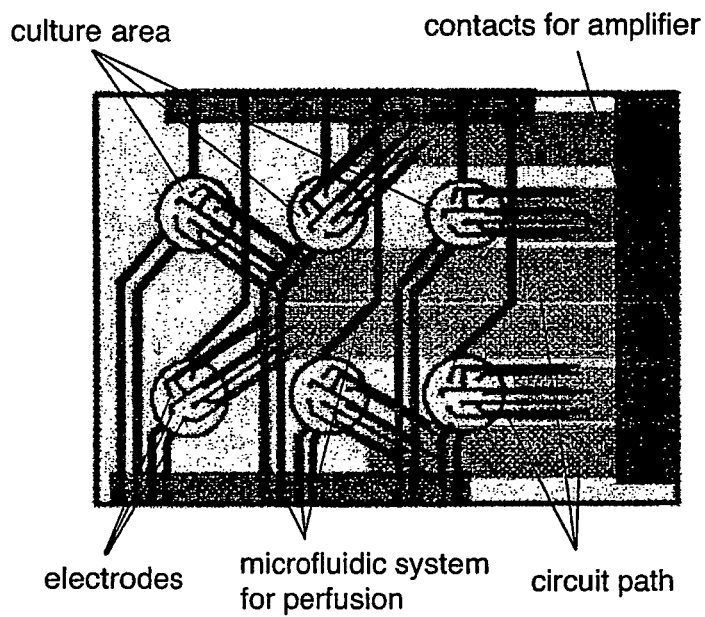
culture area
contacts for amplifier
electrodes
microfluidic system for perfusion
circuit path
B
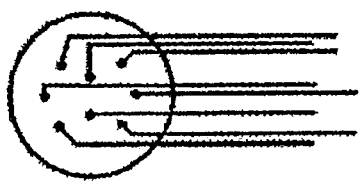

NON-INVASIVE, IN VITRO FUNCTIONAL TISSUE ASSAY SYSTEMS

FIELD OF THE INVENTION

The present invention is concerned generally with a specific combination of substrate-integrated multi-functional electrode arrays and stem cell technology.

BACKGROUND ART

Precursor cells have become a central interest in medical research. Many tissues in the body have a back-up reservoir of precursors that can replace cells that are senescent or damaged by injury or disease. Considerable effort has been made recently to isolate precursors of a number of different tissues for use in regenerative medicine and drug discovery. Sources and systems for producing differentiated cells from a stein cell population for use wherever a relatively homogenous cell population is desirable have been summarized in for example US patent application US2003/0040111. Multi- and pluripotent embryonic stem (ES) cells as well as embryonic germ (EG) cells of the mouse can be induced to differentiate in culture into a variety of cell types, including cardiac muscle cells.

Furthermore, ES cell technology is used in toxicity testing. New chemical compounds are constantly being developed and tested on animals. In addition to industrial and household chemicals, a number of chemical compositions are developed each year for use as pharmaceuticals. Rules regarding the testing of potential pharmaceuticals are promulgated by the Food and Drug Administration ("FDA"), which currently requires comprehensive testing of toxicity, mutagenicity, and other effects in at least two species before a drug candidate can be entered into human clinical trials. Preclinical toxicity testing alone costs some hundreds of thousands of dollars. Despite this huge investment, almost one third of all prospective human therapeutics fail in the first phase of human clinical trials because of unexpected toxicity. It is clear that currently available toxicological screening assays do not detect all toxicities associated with human therapy or exposure to chemicals in the environment. Better means of screening potential therapeutics or chemicals in general for potential toxicity would reduce the cost and uncertainty of developing new therapeutics and materials, for example for use in medical devices or in other devices or goods humans are exposed to every day.

The detection of teratogenic and/or embryotoxic properties of chemical agents occurs presently by determination of the reproduction toxicity of test substances following single or multi-administrations to pregnant laboratory mammals and by tests of the embryotoxicity in the early stages of pregnancy. Furthermore, in vitro tests are performed with mammal embryos (Neubert and Merker, de Gruyter, Berlin-New York (1981)) and with embryonic organs for teratogenicity tests. These test procedures have however the disadvantage that they require the use of a large number of live mammals, in particular rats and mice. In vitro test procedures, in which primary cell cultures (for example, "Limb Buds", Kochhar, Teratology 11 (1975), 273-287), or brain parts of embryonic rats (Flint and Orton, Toxicol. Appl. Pharmacol. 76 (1984), 383-395) or permanent cell lines of embryonic or adult mammal tissue, such as tumor cells of the ovary or embryonic palate cells are employed, do not fulfill, strictly speaking, the requirements which are imposed on the teratogenicity tests during the embryogenesis, namely giving indications of possible dysgenesis or developmental disturbances.

Efforts have been made for a couple of years to employ cell-based in vitro test systems for the detection of toxicity or the efficacy of new pharmaceutical compounds. Those systems depend either on primary cell cultures or on permanent cell lines. Disadvantages of primary cell cultures include laborious preparations, consumption of animals, and variation between individual animals. Permanent cell lines frequently fail to represent physiological conditions.

Hence, there remains always a need for alternative and preferably improved assays.

For example, U.S. Pat. No. 6,498,018 describes a method for determining the effect of a biological agent by contacting a cell culture with a biological agent. The cell culture contains human multipotent CNS neural stem cells that are derived from primary CNS neural tissue and a culture medium with preselected growth factors. The read-out is provided by the effect of a biological agent on the presence or absence on a biological function or property ascribable to the cell culture. A major disadvantage of this system is the fact that particular biological functions or properties inherent to a certain culture of cells are difficult to measure and often involve the destruction of a large part of the culture in order to obtain enough material for the assay.

WO02/086073 discloses a method for the positive selection of neuronal cells differentiated from nuclear transfer embryonic stem cells by taking advantage of the neural stem cell marker nectin. This method is limited to neural cell types expressing nectin naturally.

U.S. Pat. No. 6,007,993 describes an in vitro test procedure for the detection of chemically-induced embryotoxic (for example also teratogenic) effects based on differentiated pluripotent embryonic stem (ES) cells from the mouse and rat and using embryonic germ (EG) cells obtained established from primordial germ cells. Stable transgenic ES or EG stem cell clones are constructed, wherein a bacterial reporter gene, LacZ or the luciferase gene, is brought under the control of tissue-specific promoters or developmental control genes. Following differentiation of the ES cells in the presence of teratogenic substances into the different germination path derivatives, there occurs a differentiation-dependent expression in the cells, due to the activity of the tissue-specific promoters. The activation, repression or modulation of these tissue-specific genes is detected based on a reaction depending on the reporter gene employed, for example the X-Gal assay.

WO99/01552 discloses embryonic stem (ES) cells, which are transfected in a stable manner with a DNA construct encoding a non-cell damaging fluorescent protein and operatively linked thereto a cell- or development-dependent promoter. Also disclosed is a method for toxicological monitoring of substances using these ES cell cultures.

Although the above described methods employ semiquantitative as well as relatively simple and robust assays, those assays usually are limited by inhomogeneous cell populations and poor detection methods.

Thus, there is a need for cell-based in vitro assay systems that give reliable results. The solution to said technical problem is achieved by providing the embodiments characterized in the claims, and described further below.

SUMMARY OF THE INVENTION

The present invention relates to a functional cell and tissue assay system for identifying, obtaining and/or profiling a compound of interest, for example a drug, comprising:

(a) cultivating a biological material comprising cells, a cell aggregate, tissue or an organ derived from stem cells, preferably embryonic stem cells on an electrode array;
(b) subjecting said biological material to a test substance; and
(c) measuring electrical activity of said biological material through said electrode array, and optionally analyzing further parameters.

This method is preferably performed with a multi- or microelectrode array (MEA). This assay system of the present invention is a particular advantageous alternative to animal testing for cardiac effect analyses, which are usually quite time-consuming and expensive. Thus, the functional tissue assay system is particularly useful in drug development and toxicity testing of any compound a human or animal might get in contact with. A particular preferred embodiment of the functional tissue assay system of the present invention employs so-called cardiobodies, i.e. embryoid bodies (EBs) differentiated into cardiomyocytes and representing a functional cardiac tissue that consists of atrial and ventricular cardiomyocytes as well as of pacemaker cells.

In particular, the present invention provides a new technology which resides in the combination of extracellular recording of electrophysiological processes via substrate-integrated multifunctional microelectrode arrays (M-MEA) with pH electrodes, $pO_2$ electrodes and electrodes for extracellular recording of field potential of electrophysiological processes, digital optical analyses and embryonic stem cell (ES cell) technology.

Furthermore, the present invention relates to kits and apparatus useful for conducting the method of the present invention, said kits may comprise vectors or compositions of vectors, arrays, multi- or pluripotent cells, and optionally culture medium, recombinant nucleic acid molecules, standard compounds, etc.

Other embodiments of the invention will be apparent from the description that follows.

BRIEF DESCRIPTION OF THE DRAWING

The FIGURE: Chip to be used in the assay system of the present invention. A chip to be used in accordance with an assay system of the present invention can be derived from commercially available microelectrode arrays such as those described further below and in the examples. The optical part of the chip usually comprises a photographic chip, onto which the culture areas are built up with the help of light conductors or optical fibers and which serve for the recording of video sequences that can be stored in a computer and analyzed.

DEFINITIONS

For the purposes of this description, the term "stem cell" can refer to either stem cell or germ cell, for example embryonic stem (ES) and germ (EG), respectively. Minimally, a stem cell has the ability to proliferate and form cells of more than one different phenotype, and is also capable of self renewal-either as part of the same culture, or when cultured under different conditions. Embryonic stem cells are also typically telomerase positive and OCT-4 positive. Telomerase activity can be determined using TRAP activity assay (Kim et al., Science 266 (1997), 2011), using a commercially available kit (TRAPeze® XK Telomerase Detection Kit, Cat. s7707; Intergen Co., Purchase N.Y.; or TeloTAGGG™ Telomerase PCR ELISAplus, Cat. 2,013,89; Roche Diagnostics, Indianapolis). hTERT expression can also be evaluated at the mRNA level by RT-PCR. The LightCycler TeloTAGGG™ hTERT quantification kit (Cat. 3,012,344; Roche Diagnostics) is available commercially for research purposes.

In accordance with the present invention, the term embryonic stem (ES) cell includes any multi- or pluripotent stem cell derived from pre-embryonic, embryonic, or fetal tissue at any time after fertilization, and have the characteristic of being capable under appropriate conditions of producing progeny of several different cell types that are derivatives of all of the three germinal layers (endoderm, mesoderm, and ectoderm), according to a standard art-accepted test, such as the ability to form a teratoma in 8-12 week old SCID mice.

"Embryonic germ cells" or "EG cells" are cells derived from primordial germ cells. The term "embryonic germ cell" is used to describe cells of the present invention that exhibit an embryonic pluripotent cell phenotype. The terms "human embryonic germ cell (EG)" or "embryonic germ cell" can be used interchangeably herein to describe mammalian, preferably human cells, or cell lines thereof, of the present invention that exhibit a pluripotent embryonic stem cell phenotype as defined herein. Thus, EG cells are capable of differentiation into cells of ectodermal, endodermal, and mesodermal germ layers. EG cells can also be characterized by the presence or absence of markers associated with specific epitope sites identified by the binding of particular antibodies and the absence of certain markers as identified by the lack of binding of certain antibodies.

"Pluripotent" refers to cells that retain the developmental potential to differentiate into a wide range of cell lineages including the germ line. The terms "embryonic stem cell phenotype" and "embryonic stem-like cell" also are used interchangeably herein to describe cells that are undifferentiated and thus are pluripotent cells and that preferably are capable of being visually distinguished from other adult cells of the same animal.

Included in the definition of ES cells are embryonic cells of various types, exemplified by human embryonic stem cells, described by Thomson et al. (Science 282 (1998), 1145); embryonic stem cells from other primates, such as Rhesus stem cells (Thomson et al., Proc. Natl. Acad. Sci. USA 92 (1995), 7844), marmoset stem cells (Thomson et al., Biol. Reprod. 55 (1996), 254) and human embryonic germ (hEG) cells (Shamblott et al., Proc. Natl. Acad. Sci. USA 95 (1998), 13726). Other types of pluripotent cells are also included in the term. Any cells of mammal origin that are capable of producing progeny that are derivatives of all three germinal layers are included, regardless of whether they were derived from embryonic tissue, fetal tissue, or other sources. The stem cells employed in accordance with the present invention that are preferably (but not always necessarily) karyotypically normal. However, it is preferred not to use ES cells that are derived from a malignant source.

"Feeder cells" or "feeders" are terms used to describe cells of one type that are co-cultured with cells of another type, to provide an environment in which the cells of the second type can grow. The feeder cells are optionally from a different species as the cells they are supporting. For example, certain types of ES cells can be supported by primary mouse embryonic fibroblasts, immortalized mouse embryonic fibroblasts (such as murine STO cells, e.g., Martin and Evans, Proc. Natl. Acad. Sci. USA 72 (1975), 1441-1445), or human fibroblast-like cells differentiated from human ES cells, as described later in this disclosure. The term "STO cell" refers to embryonic fibroblast mouse cells such as are commercially available and include those deposited as ATCC CRL-1503.

The term "embryoid bodies" (EBs) is a term of art synonymous with "aggregate bodies". The terms refer to aggregates of differentiated and undifferentiated cells that appear when ES cells overgrow in monolayer cultures, or are maintained in suspension cultures. Embryoid bodies are a mixture of different cell types, typically from several germ layers, distinguishable by morphological criteria; see also infra. As used herein, "embryoid body", "EB" or "EB cells" typically refers to a morphological structure comprised of a population of cells, the majority of which are derived from embryonic stem (ES) cells that have undergone differentiation. Under culture conditions suitable for EB formation (e.g., the removal of Leukemia inhibitory factor or other, similar blocking factors), ES cells proliferate and form small mass of cells that begin to differentiate. In the first phase of differentiation, usually corresponding to about days 1-4 of differentiation for humans, the small mass of cells forms a layer of endodermal cells on the outer layer, and is considered a "simple embryoid body". In the second phase, usually corresponding to about days 3-20 post-differentiation for humans, "complex embryoid bodies" are formed, which are characterized by extensive differentiation of ectodermal and mesodermal cells and derivative tissues. As used herein, the term "embryoid body." or "EB" encompasses both simple and complex embryoid bodies unless otherwise required by context. The determination of when embryoid bodies have formed in a culture of ES cells is routinely made by persons of skill in the art by, for example, visual inspection of the morphology. Floating masses of about 20 cells or more are considered to be embryoid bodies; see. e.g., Schmitt et al., Genes Dev. 5 (1991), 728-740; Doetschman et al. J. Embryol. Exp. Morph. 87 (1985), 27-45. It is also understood that the term "embryoid body", "EB", or "EB cells" as used herein encompasses a population of cells, the majority of which being pluripotent cells capable of developing into different cellular lineages when cultured under appropriate conditions. As used herein, the term also refers to equivalent structures derived from primordial germ cells, which are primitive cells extracted from embryonic gonadal regions; see, e.g., Shamblott, et al. (1998), supra. Primordial germ cells, sometimes also referred to in the art as EG cells or embryonic germ cells, when treated with appropriate factors form pluripotent ES cells from which embryoid bodies can be derived; see, e.g., U.S. Pat. No. 5,670,372; Shamblott, et al., supra.

The terms "polynucleotide" and "nucleic acid molecule" refer to a polymer of nucleotides of any length. Included are genes and gene fragments, mRNA, tRNA, rRNA, ribozymes, cDNA, recombinant polynucleotides, branched polynucleotides, plasmids, vectors, isolated DNA and RNA, nucleic acid probes, and primers. As used in this disclosure, the term polynucleotides refer interchangeably to double- and single-stranded molecules. Unless otherwise specified or required, any embodiment of the invention that is a polynucleotide encompasses both a double-stranded form, and each of the two complementary single-stranded forms known or predicted to make up the double-stranded form. Included are nucleic acid analogs such as phosphoramidates and thiophosphoramidates.

A cell is said to be "genetically altered", "transfected", or "genetically transformed" when a polynucleotide has been transferred into the cell by any suitable means of artificial manipulation, or where the cell is a progeny of the originally altered cell that has inherited the polynucleotide. The polynucleotide will often comprise a transcribable sequence encoding a protein of interest, which enables the cell to express the protein at an elevated level. The genetic alteration is said to be "inheritable" if progeny of the altered cell have the same alteration.

A "regulatory sequence" or "control sequence" is a nucleotide sequence involved in an interaction of molecules that contributes to the functional regulation of a polynucleotide, such as replication, duplication, transcription, splicing, polyadenylation, translation, or degradation of the polynucleotide. Transcriptional control elements include promoters, enhancers, and repressors.

Particular gene sequences referred to as promoters, like the "αMHC" or "collagen" promoter, are polynucleotide sequences derived from the gene referred to that promote transcription of an operatively linked gene expression product. It is recognized that various portions of the upstream and intron untranslated gene sequence may in some instances contribute to promoter activity, and that all or any subset of these portions may be present in the genetically engineered construct referred to. The promoter may be based on the gene sequence of any species having the gene, unless explicitly restricted, and may incorporate any additions, substitutions or deletions desirable, as long as the ability to promote transcription in the target tissue. Genetic constructs designed for treatment of humans typically comprise a segment that is at least 90% identical to a promoter sequence of a human gene.

According to the present invention, the term "cell- and/or development-dependent promoter" is intended to mean a promoter which displays its promoter activity only in particular cell types and/or only in particular stages of cellular development, both in cell cultures (embryoid bodies) and in transgenic non-human mammals derived from the ES cells according to the invention. In addition, any other known cell-specific promoter can be employed, e.g. for nerve cells, heart cells, neurons, glia cells, hematopoietic cells, endothelial cells, smooth muscle cells, skeletal muscle cells, cartilage cells, fibroblasts and epithelial cells.

Genetic elements are said to be "operatively linked" if they are in a structural relationship permitting them to operate in a manner according to their expected function. For instance, if a promoter helps initiate transcription of the coding sequence, the coding sequence can be referred to as operatively linked to (or under control of) the promoter. There may be intervening sequence between the promoter and coding region so long as this functional relationship is maintained.

In the context of encoding sequences, promoters, and other genetic elements, the term "heterologous" indicates that the element is derived from a genotypically distinct entity from that of the rest of the entity to which it is being compared. For example, a promoter or gene introduced by genetic engineering techniques into an animal of a different species is said to be a heterologous polynucleotide. An "endogenous" genetic element is an element that is in the same place in the chromosome where it occurs in nature, although other elements may be artificially introduced into a neighboring position.

The terms "polypeptide", "peptide" and "protein" are used interchangeably in this disclosure to refer to polymers of amino acids of any length. The polymer may comprise modified amino acids, it may be linear or branched, and it may be interrupted by non-amino acids.

If not stated otherwise the terms "compound", "substance" and "(chemical) composition" are used interchangeably herein and include but are not limited to therapeutic agents (or potential therapeutic agents), food additives and nutraceuticals, agents of known toxicities such as neurotoxins, hepatic toxins, toxins of hematopoietic cells, myotoxins, carcinogens, teratogens, or toxins to one or more reproductive organs. The chemical compositions can further be agricultural chemicals, such as pesticides, fungicides, nematicides, and fertilizers, cosmetics, including so-called "cosmeceuticals", industrial wastes or by-products, or environmental contaminants. They can also be animal therapeutics or potential animal therapeutics.

Industrial products that can be tested with the methods of the present invention include bleaches, toilet, blocks, washing-up liquids, soap powders and liquids, fabric conditioners, window, oven, floor, bathroom, kitchen and carpet cleaners, dishwater detergents and rinse aids, watersoftening agents, descalers, stain removers, polishes, oil products, paints, paint removers, glues, solvents, varnishes, air fresheners, moth balls and insecticides.

New ingredients for household products are constantly being developed and needed to be tested. For example, in recent years new enzymes (to digest stains) and "optical brighteners" (which make washing appear whiter) have been developed for use in washing powders and liquids. New surfactants (which cut through grease to remove ingrained dirt) and chemical "builders" (which act as water softeners and enable surfactants to work more effectively) have been developed for use in washing powders and liquids, washing-up liquids and various cleaning agents. But also medical materials have to be tested, for example dental materials such as new filling polymers, metal alloys, and bioactive ceramic. Furthermore, chemical compositions of any part of a device, such as catheters, electrodes, adhesives, paste, gel or cream may be tested with the method of the present invention in different concentrations and with different ingredients and impurities present.

As used herein, "profile" or "profiling" of a chemical composition or compound refers to a pattern of alterations in gene or protein expression, or both, or physiological properties in an ES cell, embryoid body, tissue, etc. contacted by the chemical composition compared to a like cell, embryoid body or tissue in contact only with culture medium.

DETAILED DESCRIPTION OF THE
EMBODIMENTS OF THE PRESENT
INVENTION

The present invention relates to a functional tissue assay system for obtaining and/or profiling a compound of interest such as a drug, comprising:
(a) cultivating a biological material comprising cells, a cell aggregate, tissue or an organ derived from stem cells, preferably embryonic stem cells on an electrode array;
(b) subjecting said biological material to a test substance; and
(c) measuring electrical activity of said biological material through said electrode array, and optionally analyzing further parameters.

Preferably, the biological material is or is derived from tissue or tissue-like structures obtained by culturing an embryonic stem (ES) cell derived first cell type in the presence of at least one embryonic second cell type; and allowing integration and alignment of said at least two cell types into tissue or tissue-like structures. A corresponding method for providing a variety of tissue or tissue-like structures and like biological material is described in detail in international application WO2004/113515, the disclosure content of which is incorporated herein by reference.

In one embodiment, the biological material is derived from non-human stem cells.

The invention can be practiced using stem cells of any vertebrate species. Included are stem cells from humans; as well as non-human primates, domestic animals, livestock, and other non-human mammal. Amongst the stem cells suitable for use in this invention are primate pluripotent stem cells derived from tissue formed after gestation, such as a blastocyst, or fetal or embryonic tissue taken any time during gestation. Non-limiting examples are primary cultures or established lines of embryonic stem cells. The invention is also applicable to adult stem cells. It is referred to the literature of Anderson et al., Nat. Med. 7 (2001), 393-395 and Prockop, Science 276 (1997), 71-74, wherein the extraction and culture of those cells is described.

Media for isolating and propagating stem cells can have any of several different formulas, as long as the cells obtained have the desired characteristics, and can be propagated further. Suitable sources include Iscove's modified Dulbecco's medium (IMDM), Gibco, #12440-053; Dulbecco's modified Eagles medium (DMEM), Gibco #11965-092; Knockout Dulbecco's modified Eagles medium (KO DMEM), Gibco #10829-018; 200 mM L-glutamine, Gibco #15039-027; non-essential amino acid solution, Gibco 11140-050; [beta]-mercaptoethanol, Sigma # M7522; human recombinant basic fibroblast growth factor (bFGF), Gibco # 13256-029. Exemplary serum-containing ES medium and conditions for culturing stem cells are known, and can be optimized appropriately according to the cell type. Media and culture techniques for particular cell types referred to in the previous section are provided in the references cited herein.

As mentioned before, several sources for ES cells are at the disposal of the skilled person of which human stem cells are preferred for most of the embodiments of the present invention. Human embryonic stem cells and their use for preparing different cell and tissue types are also described in Reprod. Biomed. Online 4 (2002), 58-63. Embryonic stem cells can be isolated from blastocysts of members of the primate species (Thomson et al., Proc. Natl. Acad. Sci. USA 92 (1995), 7844). Human Embryonic Germ (EG) cells can be prepared from primordial germ cells present in human fetal material taken about 8-11 weeks after the last menstrual period. Suitable preparation methods are described in Shamblott et al., Proc. Natl. Acad. Sci. USA 95 (1998), 13726. Method for making cells that resemble embryonic stem cells or embryonic germ cells in morphology and pluripotency derived from primordial germ cells isolated from human embryonic tissue, such as from the gonadal ridges of human embryo, are described in U.S. Pat. No. 6,245,566.

Recently, is has been reported that exfoliated human deciduous tooth, a comparable very accessible tissue, contains multipotent stem cells that were identified to be a population of highly proliferative, clonogenic cells capable of differentiating into a variety of cell types including neural cells, adipocytes, and odontoblasts; see Miura et al., Proc. Natl. Acad. Sci. USA 100 (2003), 5807-5812. After in vivo transplantation, those cells were found to be able to induce bone formation, generate dentin, and survive in mouse brain along with expression of neural markers. Furthermore, multilineage potential of homozygous stem cells derived from metaphase II oocytes has been described by Lin et al. in Stem Cells 21 (2003), 152-161. Various sources of precursor cells in postnatal muscles and the factors that may enhance stem cell participation in the formation of new skeletal and cardiac muscle in vivo are reviewed in Grounds et al., J. Histochem. Cytochem. 50 (2002), 589-610. Purification of rare Hematopoietic Stem Cell(s) (HSC) to homogeneity that home to bone marrow is described in US2003/0032185. These adult bone marrow cells are described to have tremendous differentiative capacity as they can also differentiate into epithelial cells of the liver, lung, GI tract, and skin.

The field of stem cell technology is being reviewed by Kiessling and Anderson, Harvard Medical School, in Human Embryonic Stem Cells: An Introduction to the Science and Therapeutic Potential; (2003) Jones and Bartlett Publishers; ISBN: 076372341X.

Stem cells can be propagated continuously in culture, using a combination of culture conditions that promote proliferation without promoting differentiation. Traditionally, stem cells are cultured on a layer of feeder cells, typically fibroblast type cells, often derived from embryonic or fetal tissue. The cell lines are plated to near confluence, usually irradiated to prevent proliferation, and then used to support when cultured in medium conditioned by certain cells (e.g. Koopman and Cotton, Exp. Cell 154 (1984), 233-242; Smith and Hooper, Devel. Biol. 121 (1987), 1-91), or by the exogenous addition of leukemia inhibitory factor (LIF). Such cells can be grown relatively indefinitely using the appropriate culture conditions without differentiation.

In the absence of feeder cells, exogenous leukemia inhibitory factor (LIF), or conditioned medium, ES or EG cells spontaneously differentiate into a wide variety of cell types, including cells found if each of the endoderm, mesoderm, and ectoderm germ layers. With the appropriate combinations of growth and differentiation factors, however, cell differentiation can be controlled. For example, mouse ES and EG cells can generate cells of the hematopoietic lineage in vitro (Keller et al., Mol. Cell. Biol. 13 (1993), 473-486; Palacios et al., Proc. Natl. Acad. Sci. USA 92 (1995), 7530-7534; Rich, Blood 86 (1995), 463-472). Additionally, mouse ES cells have been used to generate in vitro cultures of neurons (Bain et al., Developmental Biology 168 (1995), 342-357; Fraichard et al., J. Cell Science 108 (1995), 3161-3188), cardiomyocytes (heart muscle cells) (Klug et al., Am. J. Physiol. 269 (1995), H1913-H1921), skeletal muscle cells (Rohwedel et al., Dev. Biol. 164 (1994), 87-101), vascular cells (Wang et al., Development 114 (1992), 303-316), U.S. Pat. No. 5,773,255 relates to glucose-responsive insulin secreting pancreatic beta cell lines, U.S. Pat. No. 5,789,246 relates to hepatocyte precursor cells. Hepatic differentiation of murine embryonic stem cells is also described in Jones et al., Exp. Cell Res. 272 (2002), 15-22.

Other progenitors of interest include but are not limited to chondrocytes, osteoblasts, retinal pigment epithelial cells, fibroblasts, skin cells such as keratinocytes, dendritic cells, hair follicle cells, renal duct epithelial cells, smooth and skeletal muscle cells, testicular progenitors, and vascular endothelial cells. Embryonic stem cell differentiation models for cardiogenesis, myogenesis, neurogenesis, epithelial and vascular smooth muscle cell differentiation in vitro have been generally described in Guan et al., Cytotechnology 30 (1999), 211-226.

In certain embodiments of the invention, differentiation is promoted by withdrawing one or more medium component(s) that promote(s) growth of undifferentiated cells, or act(s) as an inhibitor of differentiation. Examples of such components include certain growth factors, mitogens, leukocyte inhibitory factor (LIF), and basic fibroblast growth factor (bFGF). Differentiation may also be promoted by adding a medium component that promotes differentiation towards the desired cell lineage, or inhibits the growth of cells with undesired characteristics.

In accordance with this invention, populations of differentiated cells to be used in the assay are preferably depleted of relatively undifferentiated cells and/or of cells of undesired cell types by using a selection system that is lethal to the undesired cells and cell types, i.e. by expressing a selectable marker gene that renders cells of a specific cell type resistant to a lethal effect of an external agent, under control of a regulatory sequence that causes the gene to be preferentially expressed in the desired cell type and/or at a certain stage of development. To accomplish this, the cells are genetically altered before the process used to differentiate the cells into the desired lineage, in a way that the cells comprises a selectable marker operably linked to a first cell type specific regulatory sequence specific for the desired first cell type.

Any suitable expression vector for this purpose can be used. Suitable viral vector systems for producing stem cells altered according to this invention can be prepared using commercially available virus components. The introduction of the vector construct or constructs into the embryonic stem cells occurs in a known manner, e.g. by transfection, electroporation, lipofection or with the help of viral vectors. Viral vectors comprising effector genes are generally described in the publications referenced in the last section. Alternatively, vector plasmids can be introduced into cells by electroporation, or using lipid/DNA complexes. Exemplary is the formulation Lipofectamine 2000™, available from Gibco/Life Technologies. Another exemplary reagent is FuGENE™ 6 Transfection Reagent, a blend of lipids in non-liposomal form and other compounds in 80% ethanol, obtainable from Roche Diagnostics Corporation. Preferably, the vector constructs and transfection methods described in WO02/051987 are used; the disclosure content of which is incorporated herein by reference.

Resistance genes per se are known. Examples for these are nucleoside and aminoglycoside-antibiotic-resistance genes, e.g. puromycin (puromycin-N-acetyltransferase), streptomycin, neomycin, gentamycin or hygromycin. Further examples for resistance genes are dehydrofolate-reductase, which confers a resistance against aminopterine and methotrexate, as well as multi drug resistance genes, which confer a resistance against a number of antibiotics, e.g. against vinblastin, doxorubicin and actinomycin D.

In a particularly preferred embodiment of the present invention, said selectable marker confers resistance to puromycin. Puromycin is particularly suited for the fast elimination of non-cardiac cells in adherent culture of transgenic EBs. Furthermore, drug selection of cardiac cells can be implemented entirely in the suspension culture of transgenic EBs. Hence, it could also be shown that purified ES derived cardiomyocytes survive much longer in culture than untreated counterparts. Moreover, the elimination of undifferentiated ES cells during drug selection process has itself been shown to have clear positive effect on viability and longevity of such differentiated ES derived cells as cardiomyocytes. In addition, it could be surprisingly shown that the release from surrounding non-differentiated cells induces proliferation of cardiomyocytes. Thus, the drug selection possesses both purifying and multiplying effect.

In a preferred embodiment of the invention, said ES cell of said ES cell derived first cell type comprises a reporter gene, wherein said reporter is operably linked to a cell type specific regulatory sequence specific for said first cell type. This type of vector has the advantages of providing visualization of differentiation, definition of the time point for beginning of drug selection, visualization of drug selection and tracing of the fate of purified cells. Such vectors, which are preferably employed in accordance with the methods of the present invention are described in WO02/051987. Usually, said cell type specific regulatory sequence of the reporter gene is substantially the same as said first cell type specific regulatory sequence of the marker gene. This can advantageously be achieved by putting said marker gene and said reporter gene into the same recombinant nucleic acid molecule, i.e. vector used for stem cell transfection, preferably such that said marker gene and said reporter gene are contained on the same cistron.

The reporter can be of any kind as long as it is non-damaging for the cell and confers an observable or measurable phenotype. According to the present invention, the green fluorescent protein (GFP) from the jellyfish *Aequorea victoria* (described in WO95/07463, WO96/27675 and WO95/21191) and its derivates "Blue GFP" (Heim et al., Curr. Biol. 6 (1996), 178-182 and Redshift GFP" (Muldoon et al., Biotechniques 22 (1997), 162-167) can be used. Particularly preferred is the Enhanced Green Fluorescent Protein (EGFP). Further embodiments are the Enhanced Yellow and Cyan Fluorescent Proteins (EYFP and ECFP, respectively) and Red Fluorescent proteins (DsRed, HcRed). Further fluorescent proteins are known to the person skilled in the art and can be used according to the invention as long as they do not damage the cells. The detection of fluorescent proteins takes places through per se known fluorescence detection methods; see, e.g., Kolossov et al., J. Cell Biol. 143 (1998), 2045-2056. Alternatively to the fluorescent proteins, particularly in in vivo applications, other detectable proteins, particularly epitopes of those proteins, can also be used. Also the epitope of proteins, though able to damage the cell per se, but whose epitopes do not damage the cells, can be used; see also WO02/051987.

For the selection for stably transfected ES-cells vector constructs contain a further selectable marker gene, which confers e.g. a resistance against an antibiotic, e.g. neomycin; see also supra. Of course, other known resistance genes can be used as well, e.g. the resistance genes described above in association with the fluorescent protein encoding genes. The selection gene for the selection for stably transfected ES-cells is under the control of a different promoter than that which regulates the control of the expression of the detectable protein. Often constitutively active promoters are used, e.g. the PGK-promoter.

The use of a second selection gene is advantageous for the ability to identify the successfully transfected clones (efficiency is relatively low) at all. Otherwise a smothering majority of non-transfected ES-cell may exist and during differentiation e.g. no EGFP positive cells might be detected.

In a further embodiment of the invention the cells can be manipulated additionally so that specific tissues are not formed. This can occur for instance by inserting repressor elements, e.g. a doxizyclin inducible repressor element. Thereby, a possible contamination of the desired differentiated cells with pluripotent, potentially tumorigenic cells can be excluded.

The desired first cell type intended for the stem cell to differentiate to may be of any kind and includes but not limited to neuronal cells, glial cells, cardiomyocytes, glucose-responsive insulin secreting pancreatic beta cells, hepatocytes, astrocytes, oligodendrocytes, chondrocytes, osteoblasts, retinal pigment epithelial cells, fibroblasts, keratinocytes, dendritic cells, hair follicle cells, renal duct epithelial cells, vascular endothelial cells, testicular progenitors, smooth and skeletal muscle cells; see also supra.

In a particular preferred embodiment of the invention, said first cell type are cardiomyocytes. For this embodiment, said cell type specific regulatory sequence is preferably atrial and/or ventricular specific. Corresponding regulatory sequences, i.e. cardiac specific promoters are described in the prior art; see also supra. For example Nkx-2.5 specific for very early cardiomyocytes and mesodermal precursor cells, respectively, (Lints et al., Development 119 (1993), 419 431); human-cardiac-α-actin specific for heart tissue, (Sartorelli et al., Genes Dev. 4 (1990), 1811-1822), and MLC-2V specific for ventricular heart muscle cells (O'Brien et al., Proc. Natl. Acad. Sci. USA. 90 (1993), 5157 5161; Lee et al., Mol. Cell. Biol. 14 (1994), 1220-1229; Franz et al., Circ Res. 73 (1993), 629-638 and WO96/16163). The cardiac specific alpha-myosin heavy chain promoter is described in Palermo et al., Cell. Mol. Biol. Res. 41 (1995), 501-519 and Gulick et al., J. Biol. Chem. 266 (1991), 9180-91855. The expression of the atrial specific myosin heavy chain AMHC1 and the establishment of anteroposterior polarity in the developing chicken heart is described in Yutzey et al., Development 120 (1994), 871-883.

In accordance with this embodiment, it is preferred to use fibroblasts as said at least one embryonic second cell type. Those fibroblasts may not necessarily be derived from embryos but can also be generated de novo from ES cells in accordance with the method of the present invention. Thus, ES cells are transfected with a recombinant nucleic acid molecule comprising a marker and optionally reporter gene operatively linked to a cell type specific regulatory sequence, i.e. fibroblast specific promoter such as the a2 (I) collagen promoter though also active in bone cells; Lindahl et al., Biol. Chem. 277 (2002), 6153-6161; Zheng et al., Am. J. Pathol. 160 (2002), 1609-1617; Antoniv et al., J. Biol. Chem. 276 (2001), 21754-21764; see also Finer et al., J. Biol. Chem. 262 (1987), 13323-13333; Bou-Gharios et al., J. Cell. Biol. 134 (1996), 1333-1344; Metsaranta et al., J. Biol. Chem. 266 (1991) 16862-16869. However, for other embodiments fibroblasts may be used as well and, or alternatively, other supporting cells such as endothelial cells, etc. and derivatives thereof.

In a further preferred embodiment, the biological material employed in the assay of the present invention is obtained from culturing said at least two cell types in the presence of an embryonic or embryonic stem (ES) cell derived third cell type. Said third cell type may be any cell type mentioned above. Preferably, said third cell type are endothelial cells. Hence, either embryonic endothelial cells or ES cell derived endothelial cells may be used. In the latter embodiment, said endothelial cells are derived from ES cells transfected with a vector construct as generally described before, wherein said cell type specific regulatory sequence is an endothelial specific promoter; see, e.g., vascular endothelial-cadherin promoter described by Gory et al., Blood 93 (1999), 184-192; the Tie-2 promoter/enhancer by Schlaeger et al., Proc. Natl. Acad. Sci. USA 94 (1997), 3058-3063; the Flk-1 promoter/enhancer by Kappel et al., Biochem. Biophys. Res. Commun. 276 (2000), 1089-1099.

Further cell and tissue type specific promoters are known; see, e.g., chondrocyte specific pro-alpha1 (II) collagen chain (collagen 2) promoter fragment described by Zhou et al., J. Cell Sci. 108 (1995), 3677-3684; neural alpha-1-tubulin specific promoter described in Gloster et al., J Neurosci 14 (1994); 7319-7330 and glial fibrillary acidic protein (GFAP) promoter in Besnard et al., J. Biol. Chem. 266 (1991), 18877-18883. Furthermore, see, e.g., Kawai et al., Biochim. Biophys. Acta 1625 (2003), 246-252 and Kugler et al., Gene Ther. 10 (2003), 337-347 for glial and neuronal specific promoters. Efficiency of embryoid body formation and hematopoietic development from embryonic stem cells in different culture systems is described for example in Dang et al., Biotechnol. Bioeng. 78 (2002), 442-453.

"Tissue specific" is to be subsumed under the term "cell specific".

Further examples for non-heart specific promoters are: PECAM1, FLK-1 (endothelium), nestine (neuronal precursor cells), tyrosin-hydroxylase-1-promoter (dopaminergic neurons), smooth muscle α-actin, smooth muscle myosin (smooth muscles), α1-fetoprotein (endoderm), smooth muscle heavy chain (SMHC minimal promoter (specific for smooth muscles, (Kallmeier et al., J. Biol. Chem. 270 (1995), 30949-30957).

The term development specific promoter refers to promoters that are active during certain points of time during development. Examples for such promoters are the β-MHC promoter that is expressed during embryonal development in the ventriculum of the mouse and is superseded by the α-MHC promoter in the prenatal phase; NKx2.5, a promoter during the early mesoderm/heart development; atrial-natri-uretic-factor, a marker of the early embryonal heart with exception of the pacemaker, that is down regulated also in later developmental stages; Flk-1, an endothelium specific promoter that is active during the early vasculogenesis; intron 2-segment of the nestine gene that is expressed in neuronal precursor cells (embryonal neurons and glia cells) and adult glia cells (partially still able to divide) (Lothian and Lendahl, Eur. J. Neurosci. 9 (1997), 452-462U).

For the embodiments described hereinbefore, said resistance gene and said reporter gene are preferably contained in a bicistronic vector and are preferably separated by an IRES. Particular preferred is the use of a construct, wherein said resistance gene confers resistance to puromycin, said marker is EGFP and said promoter is the cardiac αMHC promoter.

As mentioned before, in accordance with the present invention any of said at least two cell types such as a main cell type and corresponding supporting cells may be derived from ES cells and used in the assay of the present invention. Thus, tissue or tissue-like structures to be assayed in accordance with present invention can be obtained by a method comprising the following steps:

(a) transfecting one or more multi- or pluripotent cells with recombinant nucleic acid molecules comprising a first and a second cell type specific regulatory sequence operably linked to at least one selectable marker, wherein said second cell type is different from said first cell type;
(b) culturing the cells under conditions allowing differentiation of the cells; and
(c) isolating cells of at least two differentiated cell types and/or eliminating non-differentiated cells, optionally along with cells differentiating towards irrelevant cell types from cell types of interest that activate the selectable marker in the course of differentiation.

Similarly as in the previous methods the generation of more than two cell types is desired. Therefore, the method preferably comprises transfecting said one or more cells with recombinant nucleic acid molecules comprising at least one further cell type specific regulatory sequence operably linked to at least one selectable marker, wherein said at least one further cell type is different from said first and second cell type. For use in the method, said recombinant nucleic acid molecules are comprised in the same vector or different vectors.

The cell type may be selected from the group consisting of neuronal cells, glial cells, cardiomyocytes, glucose-responsive insulin secreting pancreatic beta cells, hepatocytes, astrocytes, oligodendrocytes, chondrocytes, osteoblasts, retinal pigment epithelial cells, fibroblasts, keratinocytes, dendritic cells, hair follicle cells, renal duct epithelial cells, vascular endothelial cells, testicular progenitors, smooth and skeletal muscle cells; see also supra.

Promoters that are preferably used if the preparation of cardiac tissue is desired by differentiating the transfected stem cell(s) into cardiomyocytes, fibroblasts and optionally endothelial cells comprise those described hereinbefore. Similarly, for producing neuronal tissue one or more stem cells, for example multipotent neural stem cells, can be used and genetically engineered in accordance with the present invention to differentiate into neurons, astrocytes, and oligodendrocytes. The same rationale applies for the generation of for example liver or pancreatic tissue. Regulatory sequences of corresponding cell type specific promoters can be obtained from the literature; see, e.g., "medline" and NCBI.

The above mentioned method can be performed in different ways. First, as preferably described herein, a multiple transgenic ES clone is produced stably transfected with a certain number of vectors with a drug selection cassette driven by specific promoters accordingly to the cell types constituting the desirable tissue type. Thus, at least one of said ES cells or cell clone thereof is transfected and selected, wherein said cell or cell clone contains recombinant nucleic acid molecules with at least two different cell type specific regulatory sequences. In such a variant all emerging cell types have the origin from one common ES cell clone predecessor and the resulting ratio between different cell components depends on relative differentiation rate of each of them.

Alternatively, at least two different ES cells or clones thereof are transfected and selected, wherein said at least two different cells or cell clones contain recombinant nucleic acid molecules with different cell type specific regulatory sequences. By this approach a number of transgenic ES clones is generated where each single clone possess only one vector with drug resistant cassette driven by one of the cell type specific promoters.

For tissue modeling the relevant clones should be mixed on initial phase of differentiation ("hanging drops" or "mass culture") in order to form ES cell aggregates (EBs) where, after drug selection, emerging cell types have origin from different corresponding ES cell clones and the final ratio of the cell components also depends on and can be controlled by initial ratio between different ES cell lines. This method preferably results in cell aggregates that are chimeric embryoid bodies (EBs).

Irrespective of the particular embodiment of the assay of the invention, it is preferred that in the cells constituting the biological material to be tested at least two of said selectable markers are operably linked to said different cell type specific regulatory sequences are identical. As mentioned before, those marker or marker genes are preferably selectable markers which confer resistance to a cell toxic agent, preferably puromycin, methothrexate, or neomycin.

As described hereinbefore, said one or more of said recombinant nucleic acid molecules may further comprise a reporter operably linked to said cell type specific sequence; see supra. Herein preferred as well are the different color versions of Enhanced Green Fluorescent Protein (EGFP), in particular EYFP (yellow), ECFP (blue) and/or hcRFP (red) operably linked to different cell type specific sequences. Likewise preferred is that said selectable marker and said reporter are expressed from a bicistronic vector, preferably wherein said selectable marker and said reporter are separated one or more Internal Ribosomal Entry Sites (IRES), which are operably linked to at least one of said genes.

As mentioned above, the biological material to be tested is obtained by a method which is preferably performed such that it allows self-assembly of the different cell types, for example into the desired tissue or tissue-like structures that should reflect the tissue or organ of a mammal, preferably human, that is supposed to be exposed to a given compound. The stem cells are in a preferred embodiment of the invention available in form of aggregates that are known as embryoid bodies (EBs). WO02/051987 describes a protocol to obtain embryoid bodies. The manufacturing takes place preferably with the "hanging drop" method or by methylcellulose culture (Wobus et al., Differentiation 48 (1991), 172-182).

Alternatively to this, spinner flasks (stirring cultures) can be used as culture method. To this end, the undifferentiated ES-cells are introduced into stirring cultures and are mixed permanently according to an established procedure. Therefor, 10 million ES-cells are introduced into 150 ml medium with 20% FCS and are stirred constantly with the rate of 20 rpm., wherein the direction of the stirring motion is changed regularly. 24 hours after introduction of the ES-cells an extra 100 ml medium with serum is added and thereupon 100-150 ml of the medium is exchanged every day (Wartenberg et al., FASEB J. 15 (2001), 995-1005). Under these culture conditions large amounts of ES-cell-derived cells, i.e. cardiomyocytes, endothelial cells, neurons etc. depending on the composition of the medium can be obtained. The cells are selected by means of the resistance gene either still within the stirring culture or after plating, respectively.

Alternatively to this, the EBs differentiated in the hanging drop might be not plated, but kept simply in suspension. Even under these conditions a progression of a differentiation could be observed experimentally. The washing off of the non desired cell types can be done with mechanical mixing alone and addition of low concentration of enzyme (e.g. collagenase, trypsin); a single cell suspension is achieved with easy washing off of the non desired cell types.

In a particular preferred embodiment of the present invention, embryoid bodies are prepared according a recent developed "mass culture" system employed in the appended examples and described in detail in international application WO2005/005621.

Hence, in a particular preferred embodiment, the functional tissue assay of the present invention is performed with embryoid bodies (EBs), preferably chimeric EBs.

As mentioned before, embryoid bodies represent a complex group of cells differentiating into different tissues. In one embodiment, the cells within an embryoid body are substantially synchronized for their differentiation. Accordingly, at known intervals, the majority of the synchronized cells differentiate into the three embryonic germ layers and further differentiate into multiple tissue types, such as cartilage, bone, smooth and striated muscle, and neural tissue, including embryonic ganglia; see also Snodgrass et al., "Embryonic Stem Cells: Research and Clinical Potentials" in Smith and Sacher, eds. Peripheral Blood Stem Cells American Association of Blood Banks, Bethesda Md. (1993). Thus, the cells within embryoid bodies provide a much closer model to the complexity of whole organisms than do traditional single cell or yeast assays, while still avoiding the cost and difficulties associated with the use of mice and larger mammals. Moreover, the recent availability of human embryoid bodies improves the predictive abilities of the invention by providing an even closer vehicle for modeling toxicity and identification of drugs useful for the treatment of heart disorders in human organ systems, and in humans.

The embryoid body to be used in the assay of the invention preferably comprises a cell population, the majority of which being pluripotent cells capable of developing into different cellular lineages when cultured under appropriate conditions. It is preferred that the embryoid body comprises at least 51% pluripotent cells derived from totipotent ES cells. More preferably, the embryoid body comprises at least 75% pluripotent cells derived from totipotent ES cells. And still more preferably, the embryoid body comprises at least 95% pluripotent cells derived from totipotent ES cells.

In its simplest form, the assay of the present invention comprises creating a molecular profile involving contacting embryoid bodies on an electrode array with a chemical composition of interest, and then determining the alterations electrical activity of said biological material through said electrode array, and optionally analyzing further parameters such as those described below in the embryoid body exposed to the chemical composition (the "test embryoid body") compared to a embryoid body which was not exposed to the agent (a "control embryoid body").

The assay of the present invention can also be performed such that it allows self-assembly of the cells into the aggregates or tissue-like structures onto the array. Alternatively, the differentiated cells are dissociated from the EBs and are analyzed onto the array in cell suspension or at a single cell level; see also the Examples. Hence, in one preferred embodiment, the cells to be analyzed in the functional assay system of the present invention are obtained by dissociation from embryoid bodies (EBs), preferably by trypsinization of the cell aggregates; see also the examples.

In a particularly preferred embodiment, the method of the present invention is performed with stem cell-derived EGFP-positive cardiomyocytes, preferably ventricular-like cardiomyocytes or atrial and pacemaker-like cardiomyocytes; see also the examples.

In one embodiment, the fate of the cell types and formation of cell aggregates and tissue as well physiological and/or developmental status of the cells or cell aggregate are analyzed, before, during and/or after being exposed to the test compound, for example by isometric tension measurements, echocardiography and the like; see also infra. Preferably, the status of the cells or cell aggregates is analyzed by monitoring the differentiation of electrical activity of the cells on an array, for example by recording the extracellular field potentials with a microelectrode array (MEA). Microelectrode arrays (MEAs) are devices which allow the multiple extracellular recording of action potential generation and propagation within for example ES cell derived cardiomyocytes. These recordings resemble the well-known ECG as it is used by physicians. The matrix of the MEAs usually consists of 60 gold electrodes integrated into the bottom of a specially designed cell culture device. ES cell derived embryoid bodies (EBs) can be cultured in such devices. After attachment and spreading on the surface, the cells of the EBs containing the cardiomyocytes get in contact with the electrodes. All outcoming extracellular action potentials can then be recorded synchroneously during both short- and long time observation experiments. The following analysis of frequencies and latencies with an appropriate program allows to reveal the fine "electrical map" of the beating clusters.

For example, electrophysiological properties during the ongoing differentiation process of embryonic stem cells differentiating into cardiac myocytes can be followed by recordings of extracellular field potentials with a microelectrode array (MEA) consisting of 60 substrate-integrated electrodes has been described in Banach et al., Am. J. Physiol. Heart Circ. Physiol. 284 (2003), 2114-2123. Furthermore, Multiple arrays of tungsten microelectrodes were used to record the concurrent responses of brain stem neurons that contribute to respiratory motor pattern generation; see Morris et al., Respir. Physiol. 121 (2000), 119-133.

In a further preferred embodiment, embryoid bodies or selected, dissociated and replated in vitro differentiated cells are cultured and analyzed on fibronectin-coated cell culture dishes. In a particularly preferred embodiment, the microelectrode arrays to be used in accordance with the assay system of the present invention are coated with fibronectin; see also Example 2.

This embodiment is particularly advantageous since it could be shown that on the one hand fibronectin coating allowed the constant discrete location of the seeded cells and on the other hand did not interfere with growth and viability of the cells. Methods of coating surfaces with, for example, fibronectin are known to the person skilled in the art; see also the User Manual for the Micro-Electrode Array (MEA) of Multichannel Systems.

In a particularly preferred embodiment of the functional assay system of the present invention, the parameters frequency, mean contractility, maximum contraction amplitude and the mean area under the curve (AUC) of contractility are analyzed. Without intending to be bound by theory it is believed in accordance with the present invention that the parameters mean contractility and maximum contraction (Amplitude) reflect the physiological effects of for example β-adrenergic receptor agonists and calcium antagonists, i.e. increase and decrease of contractility and frequency, respectively, in a correct manner, while corresponding vehicle controls should not show any change.

Any substance may be tested for the above-mentioned parameters, optionally in comparison with known agonists and antagonists, respectively. From the resultant values for the parameters for example medium contractility and maximum contraction amplitude it is then possible to qualitatively and quantitatively characterize the test substance, for example, whether it is an agonist or antagonist, and whether its effect is more or less pronounced than a given standard. The method of the present invention is thus perfectly suitable for toxicity testing and profiling of compounds.

Methods for computational analysis of microarray data are known in the art; see, e.g., Quackenbush, Nature Reviews 2 (2001), 418-427 and Brazma et al., Nature Genetics 29 (2001), 365-371. Generally, statistical analysis can be done using the 2-tailed t test and considering differences to be significant at $P<0.05$ or $P<0.01$. Linear regression analysis can be performed and correlation coefficients can be determined using the program Excel 2000 (Microsoft Seattle, Wash., USA). Cluster analysis on microarray data can be performed by using for example programs available as shareware from Michael Eisen's laboratory (http://rana.l-bl.gov).

In one preferred embodiment of the method of the present invention, ES cell derived in vitro differentiated cardiomyocytes are enzymatically dissociated from cell aggregates such as EBs by trypsinization. Cardiomyocytes, preferably of a particular type, e.g. atrial and pacemaker or ventricular are selected for contractile analysis. The cardiomyocytes are loaded onto a MEA, preferably coated with fibronectin, mounted on the stage of a Zeiss Axiovert 25 (20× Objective) inverted microscope preferably through a heating adapter and continuously superfused with oxygenated physiological buffer, for example containing 132 mM NaCl, 4.8 mM KCl, 12 mM $MgCl_2$, 10 mM HEPES, 5 mM pyruvic acid, 1.8 mM $CaCl_2$, pH 7.2, at 37° C. The cardiomyocytes can be paced using a Myopacer field stimulator (IonOptix, Milton, Mass.) to produce contraction at 1, 2, 5, and 10 Hz in the absence or presence of for example 10 mM isoproterenol. An IonOptix video system (Milton, Mass.) can be used to record the cell length by two-edge detection. Data can be acquired at a sampling rate of 240 Hz and analyzed by the SoftEdge computer program from IonOptix. The data can be exported to the program Excel, and statistic analysis can be carried out using Student t test.

Hence, the assay of the invention can be used for a variety of purposes, for example for analyzing the influence of factors and compounds on tissue formation during embryonic development.

In a further embodiment, the present invention relates to arrays for use in the assay of the present invention comprising a solid support and attached thereto or suspended thereon cells, cell aggregates or tissue obtained by the method of the present invention or being in the differentiation process. The use of planar microelectrode arrays for cultured cells and cell aggregates as biosensors is of particular interest. Such arrays generally consist of a substrate of glass, plastic or silicon over which a conductor, e.g. gold, platinum, indium-tin-oxide, iridium, etc., is deposited and patterned. An insulating layer, e.g. photoresist, polyimide, silicon dioxide, silicon nitride, etc., is deposited over the conducting electrodes and interconnects and then removed in regions over the electrodes to define the recording sites. Cells are cultured directly on this surface and contact the exposed conductor at the deinsulated recording sites. Depending on the size of the electrodes and the cells, recordings of electrical activity can be from a single cell or populations of cells including cell aggregates. Each electrode site is generally connected to the input of a high input impedance, low noise amplifier, with or without AC coupling capacitors, to allow amplification of the relatively small extracellular signals. Examples of such biosensors are described by Novak et al. IEEE Transactions on Biomedical Engineering BME-33(2) (1986), 196-202; Drodge et al., J. Neuroscience Methods 6 (1986), 1583-1592; Eggers et al., Vac. Sci. Technol. B8(6) (1990), 1392-1398; Martinoia et al., J. Neuroscience Methods 48 (1993), 115-121; Maeda et al., J. Neuroscience 15 (1995), 6834-6845; and Mohr et al. Sensors and Actuators B-Chemical 34 (1996), 265-269.

An apparatus prepared and adapted for analyzing the above described arrays is also subject of the present invention.

The functional tissue assay system of the present invention is particularly suited for use in drug screening and therapeutic applications. For example, differentiated stem cells can be used to screen for factors (such as solvents, small molecule drugs, peptides, polynucleotides, and the like) or environmental conditions (such as culture conditions or manipulation) that affect the characteristics of differentiated cells. Particular screening applications of this invention relate to the testing of pharmaceutical compounds in drug research. The reader is referred generally to the standard textbook "In vitro Methods in Pharmaceutical Research", Academic Press, 1997, and U.S. Pat. No. 5,030, 015). Assessment of the activity of candidate pharmaceutical compounds generally involves combining the differentiated cells of this invention with the candidate compound, determining any change in the morphology, marker phenotype, or metabolic activity of the cells that is attributable to the compound (compared with untreated cells or cells treated with an inert compound), and then correlating the effect of the compound with the observed change. The screening may be done, for example, either because the compound is designed to have a pharmacological effect on certain cell types, or because a compound designed to have effects elsewhere may have unintended side effects. Two or more drugs can be tested in combination (by combining with the cells either simultaneously or sequentially), to detect possible drug-drug interaction effects. In some applications, compounds are screened initially for potential toxicity (Castell et al., pp. 375-410 in "In vitro Methods in Pharmaceutical Research," Academic Press, 1997). Cytotoxicity can be determined in the first instance by the effect on cell viability, survival, morphology, and expression or release of certain markers, receptors or enzymes. Effects of a drug on chromosomal DNA can be determined by measuring DNA synthesis or repair. [H]thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (pp 375-410 in "In vitro Methods in Pharmaceutical Research," Academic Press, 1997) for further elaboration.

The above mentioned parameters may be used in the functional tissue assay system of the present invention as any one of said further parameters besides the measuring of electrical activity of said biological material through said electrode array.

Preferably, embryoid bodies are used in the assays of the present invention to test the chemical composition; see also infra. The choice of the particular species from which the embryoid body is derived will typically reflect a balance of several factors. First, depending on the purpose of the study, one or more species may be of particular interest. For example, human embryoid bodies will be of particular interest for use with compositions being tested as potential human therapeutics but also for toxicological tests for substances including industrial chemicals, while equine, feline, bovine, porcine, caprine, canine, or sheep embryoid bodies may be of more interest for a potential veterinary therapeutic. Embryoid bodies of other species commonly used in preclinical testing, such as guinea pigs, mice, rat, rabbits, pigs, and dogs, are also preferred. Typically, embryoid bodies of these species will be used for "first pass" screening, or where detailed information on toxicity in humans is not needed, or where a result in a murine or other one of these laboratory species has been correlated to a known toxicity or other effect in humans. Furthermore, with respect to human therapeutics, regulatory agencies generally require animal data before human trials can begin; it will generally be desirable to use embryoid bodies of species which will be used in the preclinical animal studies. The results of toxicity testing in the embryoid bodies can then guide the researcher on the degree and type of toxicity to anticipate during the animal trials. Certain animal species are known in the art to be better models of human toxicity of different types than are others, and species also differ in their ability to metabolize drugs; see, e.g., Williams, Environ. Health Perspect. 22 (1978), 133-138; Duncan, Adv. Sci. 23 (1967), 537-541. Thus, the particular species preferred for use in a particular preclinical toxicity study may vary according to the intended use of the drug candidate. For example, a species which provide a suitable model for a drug intended to affect the reproductive system may not be as suitable a model for a drug intended to affect the nervous system. Criteria for selecting appropriate species for preclinical testing are well known in the art.

Once an embryoid body culture has been initiated, it can be contacted with a chemical composition. Conveniently, the chemical composition is in an aqueous solution, preferably in a solvent conventionally used in cell culture, for example DMSO, and is introduced to the culture medium; see also the Examples. The introduction can be by any convenient means, but will usually be by means of a pipette, a micropipettor, or a syringe. In some applications, such as high throughput screening, the chemical compositions will be introduced by automated means, such as automated pipetting systems, which may be on robotic arms. Chemical compositions can also be introduced into the medium as in powder or solid forms, with or without pharmaceutical excipients, binders, and other materials commonly used in pharmaceutical compositions, or with other carriers which might be employed in the intended use. For example, chemical compositions intended for use as agricultural chemicals or as petrochemical agents can be introduced into the medium by themselves to test the toxicity of those chemicals or agents, or introduced in combination with other materials with which they might be used or which might be found in the environment, to determine if the combination of the chemicals or agents has a synergistic effect. Typically, the cultures will be shaken at least briefly after introduction of a chemical composition to ensure the composition is dispersed throughout the medium.

The time as which a chemical composition is added to the culture is within the discretion of the practitioner and will vary with the particular study objective. Conveniently, the chemical composition will be added as soon as the embryoid body develops from the stem cells, permitting the determination of the alteration in protein or gene expression on the development of all the tissues of the embryoid body. It may be of interest, however, to focus the study on the effect of the composition on a particular tissue type. As previously noted, individual tissues, such as muscle, nervous, and hepatic tissue, are known to develop at specific times after the embryoid body has formed. Addition of the chemical composition can therefore be staged to occur at the time the tissue of interest commences developing, or at a chosen time after commencement of that development, in order to observe the effect on altering gene or protein expression in the tissue of interest.

Different amounts of a chemical composition will be used to contact an embryoid body or cell depending on the amount of information known about the toxicity of that composition, the purposes of the study, the time available, and the resources of the practitioner. A chemical composition can be administered at just one concentration, particularly where other studies or past work or field experience with the compound have indicated that a particular concentration is the one which is most commonly found in the body. More commonly, the chemical composition will be added in different concentrations to cultures of embryoid bodies or cells run in parallel, so that the effects of the concentration differences on gene or protein expression and, hence, the differences in toxicity of the composition at different concentrations, can be assessed. Typically, for example, the chemical composition will be added at a normal or medium concentration, and bracketed by twofold or fivefold increases and decreases in concentration, depending on the degree of precision desired.

Where the composition is one of unknown toxicity, a preliminary study is conveniently first performed to determine the concentration ranges at which the composition will be tested. A variety of procedures for determining concentration dosages are known in the art. One common procedure, for example, is to determine the dosage at which the agent is directly toxic. The practitioner then reduces the dose by one half and performs a dosing study, typically by administering the agent of interest at fivefold or twofold dilutions of concentration to parallel cultures of cells of the type of interest. For environmental contaminants, the composition will usually also be tested at the concentration at which it is found in the environment. For agricultural chemicals, such as pesticides which leave residues on foodstuffs, the agent will usually be tested at the concentration at which the residue is found, although it will likely be tested at other concentrations as well. Thus, the dilution of test compounds can be done by making in separated tubes a series of dilution of 50 or 100 fold concentrated compounds in DMSO. One or two µl of each dilution are distributed in each well before cell suspension distribution.

The above considerations with respect to contacting the compounds with the EBs, contacting time, etc, also apply to the assays of the invention performed on e.g. ES cells, tissue and non-human animals, if applicable.

Hence, as mentioned above the present invention relates to a functional tissue assay system for identification, obtaining and/or profiling a drug, comprising:
(a) cultivating a biological material comprising cells, a cell aggregate, tissue or an organ prepared in accordance with the present invention on an electrode array;
(b) subjecting said biological material to a test substance; and
(c) measuring electrical activity of said biological material through said electrode array, and optionally further parameters.

This assay is preferably performed with a multi- or microelectrode array (MEA), such as those mentioned above. This assay system of the present invention is a particular advantageous alternative to animal testing for cardiac affect analyses, which are usually quite time-consuming and expensive. Thus, the functional tissue assay system is particularly useful in drug development and toxicity testing of any compound a human or animal might get in contact with. Preferably, said cell aggregates are EBs; see also supra.

A particular preferred embodiment of the functional tissue assay system of the present invention employs so-called cardiobodies, i.e. embryoid bodies (EBs) differentiated into cardiomyocytes and representing a functional cardiac tissue that consists of atrial and ventricular cardiomyocytes as well as of pacemaker cells. Usually said electrode array is a multi- or microelectrode array (MEA) such as those described hereinabove.

In accordance with the assay system of the present invention, preferably any one or all of the following parameters are analyzed:
(i) $Na^+$ channels;
(ii) $Ca^{2+}/K^+$ channels;
(iii) $K^+$ channels;
(iv) Amplitude and/or Field potential duration (FDP),
(v) Chronotrophy of cardiac cells or burst periods of neuronal cells;
(vi) Arrhythmias, EAD like phenomena;
(vii) pH-value;
(viii) oxygen partial pressure (pO2);
(ix) Beating arrest; and
(x) Analysis of AV-Dissociation contractility, NO-effects and/or morphological changes.

MEAs and methods for their use in analyses of biological cells are known to the person skilled in the art. For example, international application WO97/05922 describes a micro-electrode arrangement for leaking, with local resolution, electrical cell potentials, or for electrical stimulation of networks of biological cells such as for example cell cultures, tissue slices "in vitro" or biological tissue "in vivo". A micro-element device such as described in international application WO98/22819 may be used, which has a plurality of microelements, which may be configured as microelectrodes, arranged on a substrate aid adapted for making contact to cells present in a liquid environment. The cells are guided onto the microelectrodes, are isolated or are mechanically attracted to the microelectrodes. A negative-pressure force or a hydrodynamic force may be applied on the cells. In addition, the use of an electrode array as described in international application WO01/65251 may be adapted in accordance with the teaching of the present invention.

For analyses of the multielectrode data several tools available in the prior art may be used, see for example Egert et al., "MEA-tools: An open source toolbox for the analysis of multielectrode data with MATLAB. J. Neuroscience Methods 117 (2002), 33-42, and Banach et al., Am. J. Physiol. Heart Circ. Physiol. 284 (2003), H2114-2123).

In a preferred embodiment, the biological material comprises embryoid bodies (EBs) differentiated into cardiomyocytes, most preferably EBs that consist of functional cardiac tissue that beats autonomously and covers electrophysiological properties of atrial and ventricular cardiomyocytes, as well as of pacemaker cells.

The methods and assays described herein can replace various animal models, and form novel human based tests and extreme environment biosensors. In particular, the methods of the invention can be used for toxicological, mutagenic, and/or teratogenic in vitro tests. Since the cells and tissue obtained in accordance with the present invention more closely resemble the in vivo situation the results obtained by the toxicological assays of the present invention are expected to correlate to in vivo teratogenicity of the tested compounds as well.

In a particular advantageous embodiment of the present invention, the above described assays are used as a system alternative for animal testing of cardiac effects of compounds, which is quite time consuming and expensive. This embodiment is based on "cardiobodies", i.e. embryoid bodies (EBs) differentiated into cardiomyocytes, preferably those obtainable by the method described in international application WO2005/005621. Said cardiobodies are preferably derived from mouse embryonic stem cells and consist of functional cardiac tissue that beats autonomously and covers electrophysiological properties of atrial and ventricular cardiomyocytes, as well as of pacemaker cells.

In a particular preferred embodiment, ES cells of the mouse cell line R1 (Nagy et al., Proc. Natl. Acad. Sci. 90 (1993), 8424-8428; ATCC Number SCRC-1011) or a cell line derived thereof are used in the assays of the present invention. Experiments performed in accordance with the present invention revealed that the use of cardiomyocytes derived from the murine ES cell line R1 led to a substantial improvement of the signal noise ratio of the multielectrode array system of the present invention compared to the use of cardiomyocytes derived from the D3 cell line (Doetschman et al., J. Embryol. Exp. Morphol. 87 (1985), 27-45; Proc. Natl. Acad. Sci. USA 85 (1988), 8583-8587; ATCC Number CRL-1934 and CRL-11632). Without intending to be bound by theory it is believed that the improvement of the assay is due to a better adhesion of this particular cell line on the multielectrode array.

In one embodiment, cardiobodies or cells dissociated therefrom are plated on a multielectrode array system (MEA, MultiChannel Systems, Reutlingen, Germany). Recordings of extracellular field potentials with microelectrode arrays consisting of 60 substrate-integrated electrodes can be done as described for example in Banach et al., Am. J. Physiol. Heart Circ. Physiol. 284 (2003), H2114-2123. Extracellular recordings of the field potential reflect the electrophysiological changes during excitation of the cardiomyocytes in cardiobodies. In a particular preferred embodiment, automated analysis is performed using the AxioTools software developed by the Axiogenesis AG, Cologne, Germany.

The assay of the present invention was evaluated with compounds with known effects an ion channels present in cardiac tissue, for example cisapride, lidocaine, isoproterenol and nifedipine, which were tested either in the assay of the present invention or in rabbit Langendorff preparations. All compounds showed similar results in both test systems as well as a correlation in Patch Clamp and MEA analysis, which leads to the implementation of the assay of the present invention in the cardiac safety screening routine. In order to achieve most reliable results, preferably most if not all of the following parameters are analyzed, if applicable:
(i) $Na^+$ channels;
(ii) $Ca^{2+}/K^+$ channels;
(iii) $K^+$ channels;
(iv) Amplitude and/or Field potential duration (FDP);
(v) Chronotrophy of cardiac cells or burst periods of neuronal cells;
(vi) Arrhythmias, EAD like phenomena;
(vii) pH-value;
(viii) oxygen partial pressure (pO2);
(ix) Beating arrest; and
(x) Analysis of AV-Dissociation contractility, NO-effects and/or morphological changes.

The advantages of this particular embodiment of screening assays of the present invention over conventional in-vitro assays include
   highly standardized cell culture model, homogeneous and reproducible production of cardiobodies;
   presence of atrial, ventricular, and pacemaker cells with normal physiological behavior (e.g. expression and regulation of ion channels);
   ECG-like screening of all electrophysiological properties of the cardiobody including effects on all ion channels, chroriotropy and appearance of arrhythmias;
   entirely in vitro-based system, no requirement for laborious cell preparation
   time- and cost-saving Thus, in the various assays of the present invention compounds, in particular cardiac active compounds can be tested in accordance with methods described in DE 195 25 285 A1; Seiler et al., ALTEX 19 Suppl 1 (2002), 55-63; Takahashi et al., Circulation 107 (2003), 1912-1916 and Schmidt et al., Int. J. Dev. Biol. 45 (2001), 421-429; the latter describing ES cell test (EST) used in a European Union validation study for screening of embryotoxic agents by determining concentration-dependently the differentiation of ES cells into cardiac and myogenic cells.

Cells and tissue of the central nervous system (CNS) generated by the methods of the present invention or during differentiation is said methods can be tested, for example, in cell culture such as described in U.S. Pat. No. 6,498,018. Similarly, cells and tissue related to the liver can be tested; see, e.g., US2003/0003573. A further in vitro test procedure for the detection of chemically induced effects on embryonic development and for differentiation for the purpose of embryotoxicity/teratogenicity screening based on differentiated pluripotent embryonic stem (ES) cells from mice and rats using embryonic germ (EG) cells obtained from primordial germ cells is described in WO97/01644 and can be adapted in accordance with teachings of the present invention.

Cells and tissue of the CNS may also be analyzed using an electrode array as described above. Means and methods for analyzing regulatory interactions of neuronal activity of cells and tissue cultures on microelectrode arrays are known to the person skilled in the art; see for example van Bergen et al., Brain Res Brain Res. Protocol 2003/11 (2003), 123-133 and international application WO01/65251.

Preferred compound formulations for testing do not include additional components, such as preservatives, that have a significant effect on the overall formulation; see also supra. Thus preferred formulations consist essentially of a biologically active compound and a physiologically acceptable carrier, e.g. water, ethanol, DMSO, etc. However, if a compound is liquid without an excipient the formulation may consist essentially of the compound itself.

Furthermore, a plurality of assays may be run in parallel with different compound concentrations to obtain a differential response to the various concentrations. As known in the art, determining the effective concentration of a compound typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection.

Compounds of interest encompass numerous chemical classes, though typically they are organic molecules; see also supra. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Compounds and candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. For example, inhibition of tumor-induced angiogenesis and matrix-metalloproteinase expression in confrontation cultures of embryoid bodies and tumor spheroids by plant ingredients used in traditional chinese medicine has been described by Wartenberg et al. in Lab. Invest. 83 (2003), 87-98.

Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

The compounds may also be included in a sample including fluids to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1 µl to 1 ml of a biological sample is sufficient.

Test compounds include all of the classes of molecules described above, and may further comprise samples of unknown content. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest compounds being assessed for potential therapeutic value, i.e. drug candidates.

The test compound may optionally be a combinatorial library for screening a plurality of compounds. Such a collection of test substances can have a diversity of about $10^3$ to about $10^5$ is successively reduced in running the method, optionally combined with others twice or more. Compounds identified in the method of the invention can be further evaluated, detected, cloned, sequenced, and the like, either in solution or after binding to a solid support, by any method usually applied to the detection of a specific DNA sequence such as PCR, oligomer restriction (Saiki et al., Bio/Technology, 3 (1985), 1008-1012>, allele-specific oligonucleotide (ASO) probe analysis (Conner et al., Proc. Natl. Acad. Sci. USA, 80 (1983), 278), oligonucleotide ligation assays (OLAs) (Landegren et al., Science, 241 (1988), 1077), and the like. Molecular techniques for DNA analysis have been reviewed (Landegren et al., Science, 242 (1988), 229-237). Hence, the method of the present invention can also be used for transcriptional profiling of embryonic and adult stem cells; see, e.g., Ramalho-Santos et al., Science 298 (2002), 597-600; Tanaka et al., Genome Res. 12 (2002), 1921-1928.

Incubating includes conditions which allow contact between the test compound and the ES cell or ES derived cells. As described above, it is be desirable to test an array of compounds or small molecules on a single or few ES cells on a "chip" or other solid support. For example, cardiomyocytes or neurons on chips would give a readout of the rate of contraction or number of firings, respectively, in response to a compound and for the detection of harmful or at least biologically active environmental agents.

Neuronal biologically compatible electrode arrays allow the stem cells to undergo further differentiation on the array itself. These arrays allow the measurement of real time changes in electrical activity in the ES derived neurons in response to the presence of known or unidentified agents. The electrical activity of cardiomyocytes can be monitored by plating the cells on an array of extracellular microelectrodes (Connolly et al., Biosens. Biores. 5 (1990), 223-234). The cells show regular contractions, and the extracellular signal recorded showed a relationship to intracellular voltage recordings (Connolly et al., supra). This noninvasive method allows long term monitoring and is simpler and more robust than typical whole cell patch clamp techniques.

The assay of the present invention is particularly suited to provide modulation reference patterns and databases of modulation reference patterns for a wide range of biologically active compounds. The reference patterns are then used for the identification and classification of test compounds. Evaluation of test compounds may be used to achieve different results.

Methods for the classification of biological agents according to the spectral density signature of evoked changes in cellular electric potential are known to the person skilled in the art; see, e.g., U.S. Pat. No. 6,377,057. Thus, biologically active compounds are classified according to their effect on ion channels, changes in membrane potential and ionic currents, and the frequency content of action potentials that the compound(s) evoke in excitable cells. The spectral density changes of such evoked membrane potential or action potential are a characteristic for each channel type that is modulated by the test compound. A pattern of spectral changes in membrane potential is determined by contacting a responsive cell with a compound, and monitoring the membrane potential or ionic currents over time. These changes correlate with the effect of that compound, or class of compounds, on the ion channels of the responding cell. This pattern of spectral changes provides a unique signature for the compound, and provides a useful method for characterization of channel modulating agents.

The effect of a compound on ion channels, and on the action potential of a living cell, can provide useful information about the classification and identity of the compound. Methods and means for extracting such information are of particular interest for the analysis of biologically active compounds, with specific applications in pharmaceutical screening, drug discovery, environmental monitoring, biowarfare detection and classification, and the like.

Examples of whole cell based biosensors are described in Gross et al., Biosensors and Bioelectronics 10 (1995), 553-567; Hickman et al. Abstracts of Papers American Chemical Society 207 (1994), BTEC 76; and Israel et al. American Journal of Physiology: Heart and Circulatory Physiology 27 (1990), H1906-H1917.

Connolly et al., Biosens. Biores. 5 (1990), 223-234 describe a planar array of microelectrodes developed for monitoring the electrical activity of cells in culture. The device allows the incorporation of surface topographical features in an insulating layer above the electrodes. Semiconductor technology is employed for the fabrication of the gold electrodes and for the deposition and patterning of an insulating layer of silicon nitride. The electrodes were tested using a cardiac cell culture of chick embryo myocytes, and the physical beating of the cultured cells correlated with the simultaneous extracellular voltage measurements obtained.

The molecular control of cardiac ion channels is reviewed by Clapham, Heart Vessels Suppl. 12 (1997), 168-169. Oberg and Samuelsson, J. Electrocardiol. 14 (1981), 13942, perform fourier analysis on the repolarization phases of cardiac action potentials. Rasmussen et al. American Journal of Physiology 259 (1990), H370-H389, describe a mathematical model of electrophysiological activity in bullfrog atria.

A large body of literature exists in the general area of ion channels. A review of the literature may be found in the series of books, "The Ion Channel Factsbook", volumes 1-4, by Edward C. Conley and William J. Brammar, Academic Press. An overview is provided of: extracellular ligand-gated ion channels (ISBN: 0121844501), intracellular ligand-gated channels (ISBN: 012184451X), inward rectifier and intercellular channels (ISBN: 0121844528), and voltage gated channels (ISBN: 0121844536). Hille, B. (1992) "Ionic Channels of Excitable Membranes", 2.sup.nd Ed. Sunderland Mass.: Sinauer Associates, also reviews potassium channels.

In another aspect, the biological material is screened for bioactive substances. In one example, the cells are coupled with a substrate such that electrophysiological changes in the cells in response to external stimuli can be measured, e.g., for use as a high-throughput screen for bioactive substances. The cells can also be transfected with DNA that targets, expresses, or knocks-out specific genes or gene products in the cell. By providing such chip-mounted cells coupled with measuring devices, such as a computer, many compounds can be screened rapidly and accurately. The cells or chips could also be coupled to the measuring device in arrays for large-scale parallel screening.

The assay methods of the present invention can be in conventional laboratory format or adapted for high throughput. The term "high throughput" (HTS) refers to an assay design that allows easy analysis of multiple samples simultaneously, and capacity fox robotic manipulation. Another desired feature of high throughput assays is an assay design that is optimized to reduce reagent usage, or minimize the number of manipulations in order to achieve the analysis desired.

In another preferred embodiment, the method of the present invention comprises taking 2, 3, 4, 5, 7, 10 or more measurements, optionally at different positions within the array. In one embodiment of the screening methods of the present invention a compound known to activate or inhibit differentiation process and/or tissue structure formation is added to the sample or culture medium, for example retinoic acid; for appropriate compounds see also supra.

Furthermore, the above-described methods can, of course, be combined with one or more steps of any of the above-described screening methods or other screening methods well known in the art. Methods for clinical compound discovery comprises for example ultrahigh-throughput screening (Sundberg, Curr. Opin. Biotechnol. 11 (2000), 47-53) for lead identification, and structure-based drug design (Verlinde and Hol, Structure 2 (1994), 577-587) and combinatorial chemistry (Salemme et al., Structure 15 (1997), 319-324) for lead optimization. Once a drug has been selected, the method can have the additional step of repeating the method used to perform rational drug design using the modified drug and to assess whether said modified drug displays better affinity according to for example interaction/energy analysis. The method of the present invention may be repeated one or more times such that the diversity of said collection of compounds is successively reduced.

Substances are metabolized after their in vivo administration in order to be eliminated either by excretion or by metabolism to one or more active or inactive metabolites (Meyer, J. Pharmacokinet. Biopharm. 24 (1996), 449-459). Thus, rather than using the actual compound or drug identified and obtained in accordance with the methods of the present invention a corresponding formulation as a pro-drug can be used which is converted into its active form in the patient by his/her metabolism. Precautionary measures that may be taken for the application of pro-drugs and drugs are described in the literature; see, for review, Ozama, J. Toxicol. Sci. 21 (1996), 323-329.

Furthermore, the present invention relates to the use of a compound identified, isolated and/or produced by any of these methods for the preparation of a composition for the treatment of disorders related to, for example damaged tissue or aberrant tissue or organ formation, heart insufficiency, etc.; see also supra. Preferably, the isolated compound or corresponding drug supports wound healing and/or healing of damaged tissue. As a method for treatment the identified substance or the composition containing it can be administered to a subject suffering from such a disorder. Compounds identified, isolated and/or produced by the method described above can also be used as lead compounds in drug discovery and preparation of drugs or prodrugs. This usually involves modifying the lead compound or a derivative thereof or an isolated compound as described hereinbefore such as modifying said substance to alter, eliminate and/or derivatize a portion thereof suspected causing toxicity, increasing bioavailability, solubility and/or half-life. The method may further comprise mixing the substance isolated or modified with a pharmaceutically acceptable carrier. The various steps recited above are generally known in the art. For example, computer programs for implementing these techniques are available; e.g., Rein, Computer-Assisted Modeling of Receptor-Ligand Interactions (Alan Liss, New York, 1989). Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, New York, USA. Furthermore, peptidomimetics and/or computer aided design of appropriate derivatives and analogues can be used, for example, according to the methods described above. Methods for the lead generation in drug discovery also include using proteins and detection methods such as mass spectrometry (Cheng et al., J. Am. Chem. Soc. 117 (1995), 8859-8860) and some nuclear magnetic resonance (NMR) methods (Fejzo et al., Chem. Biol. 6 (1999), 755-769; Lin et al., J. Org. Chem. 62 (1997), 8930-8931). They may also include or rely on quantitative structure-action relationship (QSAR) analyses (Kubinyi, J. Med. Chem. 41 (1993), 2553-2564, Kubinyi, Pharm. Unserer Zeit 23 (1994), 281-290) combinatorial biochemistry, classical chemistry and others (see, for example, Holzgrabe and Bechtold, Pharm. Acta Helv. 74 (2000), 149-155). Furthermore, examples of carriers and methods of formulation may be found in Remington's Pharmaceutical Sciences.

Once a drug has been selected in accordance with any one of the above-described methods of the present invention, the drug or a pro-drug thereof can be synthesized in a therapeutically effective amount. As used herein, the term "therapeutically effective amount" means the total amount of the drug or pro-drug that is sufficient to show a meaningful patient benefit, i.e., treatment, healing, prevention or amelioration of damaged tissue, or an increase in rate of treatment, healing, prevention or amelioration of such conditions. In addition or alternatively, in particular with respect to pre-clinical testing of the drug the term "therapeutically effective amount" includes the total amount of the drug or pro-drug that is sufficient to elicit a physiological response in a non-human animal test.

In one embodiment, the method of the invention further comprises mixing the substance isolated or modified with a pharmaceutically acceptable carrier. Examples of carriers and methods of formulation may be found in Remington's Pharmaceutical Sciences.

As mentioned above, the methods and assays of the present invention can be used for toxicological, embryotoxic, mutagenic, and/or teratogenic in vitro tests; see supra. Another important aspect of the present invention is therefore a method of determining toxicity, preferably teratogenicity, embryotoxicity, chronic or acute toxicity of a compound comprising the steps of the methods described herein.

The assays may be simple "yes/no" assays to determine whether there is a responsive change compared to a control. The test compound or a plurality of test compounds can also be subjected to the test cell, preferably embryoid body in different concentrations or dilution series, preferably at doses that correspond to physiological levels of the corresponding type of test compounds. It is thus also possible to easy generate compound profiles in purpose similar to those described in WO00/34525. For example, two or more assays may be used and/or parameters may be assessed. Those assays/parameters can be performed/assessed in parallel or subsequently; or the results of one assay may be compared with results of a corresponding assay performed elsewhere. Thus, a molecular profile of a test chemical composition can be established by detecting the alterations in the "electrical activity" in, for example, embryoid bodies contacted by the test chemical composition as described in previous sections. Once the molecular profile of the test composition is determined, it can be compared to that of a chemical composition with predetermined toxicities or, preferably, to a library of molecular profiles of chemical compositions with predetermined toxicities. The outcome of such comparison provide information for one to predict the likelihood of whether the test composition is toxic, what type of toxicities, and how toxic it would be as compared to the other known toxic compositions.

For the purpose of practicing the invention, the predictions of toxicity of the test composition based on its molecular profiles in ES cells, tissue, etc, preferably EB cells does not have to be 100% accurate. To have a major positive impact on the efficiency and costs of drug development, one only has to modestly increase the probability that the less toxic and thus more successful drug candidates are, for example, on the top half of a prioritized list of new drug leads.

Since the cells and tissue obtained in accordance with the present invention more closely resemble the in vivo situation compared to conventional cell based assays, the results obtained by the assays of the present invention are expected to correlate to in vivo teratogenicity or embryotoxicity of the tested compounds as well.

Several test substances can be combined and either added simultaneously or sequentially to gain information about possible enhancing or quenching effects. Thus a further aspect of the invention relates to the method described previously, wherein said contacting step further includes contacting said test sample with at least one second test substance in the presence of said first test substance. Two or more substances tested in combination will provide information about their interaction in general.

A preferred embodiment of the methods according to the present invention involves adding a compound known to activate or inhibit differentiation process to the culture medium, particularly if this test substance is a therapeutic agent or a mixture thereof. This screening may be done, for example, either because the compound is known to have a effect on the differentiation of certain cell types and is tested to determine its potential for guiding the differentiation of other cell types, or because a compound designed to have effects elsewhere may have unintended side effects. The last aspect applies particularly to therapeutic agents.

The present invention also relates to kit compositions containing specific reagents such as those described hereinbefore useful for conducting any one of the above described methods of the present invention, containing the vector or the composition of vectors described hereinbefore, multi- or pluripotent cells, and optionally culture medium, recombinant nucleic acid molecules, standard compounds, etc. Such a kit would typically comprise a compartmentalized carrier suitable to hold in close confinement at least one container. The carrier would further comprise reagents useful for performing said methods. The carrier may also contain a means for detection such as labeled enzyme substrates or the like.

Furthermore, the present invention relates to a chip comprising an electrode array as defined hereinabove. In a particularly preferred embodiment, the present invention relates to arrays and chips comprising a solid support and attached thereto or suspended thereon cells, cell aggregates or tissue obtained by the method of the present invention or being in the differentiation process. Such arrays generally consist of a substrate of glass, plastic or silicon on which the test cells aggregates or tissues are deposited in a particular pattern. Depending on the type of array, these might additionally be covered by a conductor, e.g. gold, platinum, indium-tin-oxide, iridium, etc., which allows a direct measurement by employing the conductivity of cells. The use of such planar microelectrode arrays for cultured cells and cell aggregates as biosensors is of particular interest.

Preferably, the chip of the present invention is characterized by the presence of embryoid bodies or cardiomyocytes obtainable by the methods of the present invention described herein and illustrated in the Examples. In a particular preferred embodiment, the chip of the present invention comprises cardiobodies, i.e. cardiac-like tissues including atrial and ventricular cardiomyocytes as well as pacemaker cells. In a particular preferred embodiment, said chip comprises a surface as illustrated in the FIGURE.

In addition, the present invention relates to an apparatus for use in the methods and assays of the present invention described herein. For example, a cell-potential measurement apparatus having a plurality of microelectrodes and which may be used and/or adapted in accordance with the teaching of the present invention is described in European patent application EP 0 689 051 A3.

Furthermore, international application WO98/54294 describes an apparatus and method for monitoring cells and a method for monitoring changes in cells upon addition of an analyte to the cell's environment, comprising a device which includes an array of microelectrodes disposed in a cell culture chamber, upon which array a portion of cells adhere to the surfaces of the microelectrodes. The diameter of the cells are larger than the diameters of the microelectrodes. A voltage signal is applied across each of the microelectrodes and a reference electrode. Detection and monitoring of the signals resulting from the application of the voltage signal provides information regarding the electrical characteristics of the individual cells, including impedance (combined cell membrane capacitance and conductance), action potential parameters, cell membrane capacitance, cell membrane conductance, and cell/substrate seal resistance.

Further means and methods that may be implemented in accordance with the teaching of the present invention can be found in the literature, see for example Egert et al., Brain Res. Brain Res. Protoc. 2 (1998), 229-242; Duport et al., Biosens. Bioelectron. 14 (1999), 369-376 and German patent application DE 195 29 371 A1.

Hence, the means and methods of the present invention described herein-before can be used in a variety of applications including but not limited to "loss of function" assays with ES cells containing homozygous mutations of specific genes, "gain of function" assays with ES cells overexpressing exogenous genes, developmental analysis of teratogenic/embryotoxic compounds in vitro, pharmacological assays and the establishment of model systems for pathological cell functions, and application of differentiation and growth factors for induction of selectively differentiated cells which, can be used as a source for tissue grafts; see for review, e.g., Guan et al., Altex 16 (1999), 135-141.

Yet another aspect of the present invention relates to a method of conducting a drug discovery business, comprising:

providing one or more assay systems or components thereof as described herein for identifying a drug candidate; and/or conducting therapeutic profiling of drugs identified in the previous step, or further analogs thereof, for efficacy and toxicity according to the assays of the present invention; and formulating a pharmaceutical preparation including one or more drugs identified in the previous step as having an acceptable therapeutic profile.

Utilizing the methods described above, the identity of a drug is determined. Agents are identified by their ability to alter the certain parameters such as those described hereinbefore, e.g. those described for MEAs. For suitable lead compounds that are identified, further therapeutic profiling of the agent, or analogs thereof, can be carried out for assessing efficacy and toxicity in animals. Those compounds having therapeutic profiles after animal testing can be formulated into pharmaceutical preparations for use in humans or for veterinary uses. The subject business method can include an additional step of establishing a distribution system for distributing the pharmaceutical preparation for sale, and may optionally include establishing a sales group for marketing the pharmaceutical preparation.

Instead of developing the identified drug in house, further drug development can also be achieved by a different company. Thus a further aspect of the present invention relates to a method of conducting a target discovery business comprising:

providing one or more assay systems described herein or components thereof for identifying a drug;

alternatively or in addition conducting therapeutic profiling of drugs for efficacy and toxicity according to the assays of the present invention; and licensing, to a third party, the rights for further drug development and/or sales for drugs identified or profiled, or analogs thereof.

For suitable lead compounds that have been identified, further profiling of the agent, or further analogs thereof, can be carried out for assessing efficacy and toxicity in animals, depending on the modalities of the agreement with the respective third party. Further development of those compounds for use in humans or for veterinary uses will then be conducted by the third party. The subject business method will usually involve either the sale or licensing of the rights to develop said compound but may also be conducted as a service, offered to drug developing companies for a fee.

The present invention also relates to drugs identified according to the methods and assays described above as well as to pharmaceutical compositions for use in therapy comprising such a drug.

The drug according to the invention can be combined with suitable diluents or carriers, preferably those which are pharmaceutically acceptable. Examples of such carriers, diluents and methods of formulation may be found in Remington's Pharmaceutical Sciences. To form a pharmaceutically acceptable composition suitable for effective administration, such compositions will contain an effective amount of the modulator. Carriers or diluents are usually sterile and non-toxic, and defined as vehicles commonly used to formulate pharmaceutical compositions for animal or human administration. The diluent is selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. A therapeutically effective dose refers to that amount of modulator which is sufficient to achieve the desired effect on differentiation of target cells.

Further examples of suitable pharmaceutical carriers are well known in the art and include phosphate buffered saline solutions, emulsions, such as oil/water emulsions, various types of wetting agents, sterile solutions etc. Compositions comprising such carriers can be formulated by well known conventional methods. Accordingly, the present invention also provides a method of making a pharmaceutical composition for use in modulating cell differentiation comprising mixing a modulator of cell differentiation identified according to a method of the invention with a suitable diluent or carrier.

The above disclosure generally describes the present invention. A more complete under-standing can be obtained by reference to the following specific examples which are provided herein for purposes of illustration only and are not intended to limit the scope of the invention.

These and other embodiments are disclosed and encompassed by the description and examples of the present invention. Further literature concerning any one of the materials, methods, uses and compounds to be employed in accordance with the present invention may be retrieved from public libraries and databases, using for example electronic devices. For example the public database "Medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness is given in Berks, TIBTECH 12 (1994), 352-364.

The above disclosure generally describes the present invention. A more complete under-standing can be obtained by reference to the following specific examples and FIGURE which are provided herein for purposes of illustration only and are not intended to limit the scope of the invention. The contents of all cited references (including literature references, issued patents, published patent applications as cited throughout this application and manufacturer's specifications, instructions, etc) are hereby expressly incorporated by reference; however, there is no admission that any document cited is indeed prior art as to the present invention.

The practice of the present invention will employ, unless otherwise indicated, conventional techniques of cell biology, cell culture, molecular biology, transgenic biology, microbiology, recombinant DNA, and immunology, which are within the skill of the art. For further elaboration of general techniques concerning stem cell technology, the practitioner can refer to standard textbooks and reviews, for example Teratocarcinomas and embryonic stem cells: A practical approach (E. J. Robertson, ed., IRL Press Ltd. 1987); Guide to Techniques in Mouse Development (P. M. Wasserman et al., eds., Academic Press 1993); Embryonic Stem Cell Differentiation in Vitro (Wiles, Meth. Enzymol. 225 (1993), 900); Properties and uses of Embryonic Stem Cells: Prospects for Application to Human Biology and Gene Therapy (Rathjen et al., Reprod. Fertil. Dev. 10 (1998), 31). Differentiation of stem cells is reviewed in Robertson, Meth. Cell Biol. 75 (1997), 173; and Pedersen, Reprod. Fertil. Dev. 10 (1998), 31. Besides the sources for stem cells described already above further references are provided; see Evans and Kaufman, Nature 292 (1981), 154-156; Handyside et al., Roux's Arch. Dev. Biol., 196 (1987), 185-190; Flechon et al., J. Reprod. Fertil. Abstract Series 6 (1990), 25; Doetschman et al., Dev. Biol. 127 (1988), 224-227; Evans et al., Theriogenology 33 (1990), 125-128; Notarianni et al., J. Reprod. Fertil. Suppl., 43 (1991), 255-260; Giles et al., Biol. Reprod. 44 (Suppl. 1) (1991), 57; Strelchenko et al., Theriogenology 35 (1991), 274; Sukoyan et al., Mol. Reprod. Dev. 93 (1992), 418-431; Iannaccone et al., Dev. Biol. 163 (1994), 288-292. Methods in molecular genetics and genetic engineering are described generally in the current editions of Molecular Cloning: A Laboratory Manual, (Sambrook et al., (1989) Molecular Cloning: A Laboratory Manual, 2nd ed., Cold Spring Harbor Laboratory Press); DNA Cloning, Volumes I and II (D. N. Glover ed., 1985); Oligonucleotide Synthesis (M. J. Gait ed., 1984); Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Gene Transfer Vectors for Mammalian Cells (Miller & Calos, eds.); Current Protocols in Molecular Biology and Short Protocols in Molecular Biology, 3rd Edition (F. M. Ausubel et al., eds.); and Recombinant DNA Methodology (R. Wu ed., Academic Press). Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.); Immobilized Cells And Enzymes (IRL Press, 1986); B. Perbal, A Practical Guide To Molecular Cloning (1984); the treatise, Methods In Enzymology (Academic Press, Inc., N.Y.); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986). Reagents, cloning vectors, and kits for genetic manipulation referred to in this disclosure are available from commercial vendors such as BioRad, Stratagene, Invitrogen, and ClonTech. General techniques in cell culture and media collection are outlined in Large Scale Mammalian Cell Culture (Hu et al., Curr. Opin. Biotechnol. 8 (1997), 148); Serum-free Media (Kitano, Biotechnology 17 (1991), 73); Large Scale Mammalian Cell Culture (Curr. Opin. Biotechnol. 2 (1991), 375); and Suspension Culture of Mammalian Cells (Birch et al., Bioprocess Technol. 19 (1990), 251). Other observations about the media and their impact on the culture environment have been made by Marshall McLuhan and Fred Allen.

EXAMPLES

Example 1

Differentiation Protocol for ES Cells for the Preparation of Ventricular Cardiomyocytes and MEA Recording For differentiation of ES cells into ventricular cardiomyocytes ES cells of cell line R1 (see supra and, e.g., Nagy et al., Proc. Natl. Acad. Sci. 90 (1993), 8424-8428) were cultured on 10 cm Petri dishes in Dulbecco's-modified Eagle's medium (DMEM) supplemented with 15% fetal calf serum (FCS) and leukemia inhibitory factor (LIF) on a layer of feeder cells (irradiated mouse embryonic fibroblasts). Cells were incubated at 37° C., 7% $CO_2$ and 95% humidity.

Day 0: Cells were trypsinized to a single cell suspension and collected by centrifugation. Cells were resuspended to a density of approximately $2 \times 10^6$ cells per ml in Knock-Out (KO) medium supplemented with 15% serum replacement (SR). 4 ml per 6 cm Petri dish of this suspension were incubated on a rocking table at 50 rpm, 37° C., 5% $CO_2$ and 95% humidity for the following day;

Day 1: Dilution of the ES cell aggregates (embryonic bodies; EBs) in KO medium supplemented with 15% SR to a density of 2000 EBs/10 ml and further incubation;

Day-3: Change of medium (MW) with KO medium supplemented with 15% SR;

Day 4: MW onto Iscove's medium supplemented with 20% FCS;

Day 5: MW with Iscove's medium supplemented with 20% FCS;

Day 6: MW onto KO medium supplemented with 15% SR;

Day 7: For use of the EBs in the MEA assay of the invention, EBs were plated in 100 µl Iscove's medium supplemented with 15% FCS with 1 EB per culture area and sealed with a polydimethylsilane (PDMS) closure and used for the assay from Day 10 onwards.

For the preparation of cardiac tissue for the assay recombinant ES cells, which express the puromycin resistance gene under the control of the heart-specific promoters (alpha MHC for atrial and pacemaker cells or RLC-2v for ventricular cells), were subjected on Day 9 to 2 µg puromycin/ml and incubated for further three days. After dissociation of the cells with collagenase on Day 12 cardiac cells were mixed with embryonic fibroblasts in a ratio of 1:1 and seeded on the multielectrode array with a density of $3 \times 10^5$ cells per $cm^2$. After the following three days a cardiac-like tissue develops, which can be analyzed in the multielectrode assay of the invention. For example, substrate-integrated, planar MEAs (Multi Channel Systems, Reutlingen, Germany) for long-term recordings of the spontaneous electrical activity from cultures of cardiac myocytes and EBs can be used; see also Egert et al., (1998) and Banach et al., (2003), and references cited therein. EBs can be positioned in the middle of a sterilized MEA consisting of 60 Titanium Nitride coated gold electrodes (Ø=30 µm; inter-electrode distance 200 µm in a square grid). For recording, a separate sterile Ag/AgCl electrode can be temporarily inserted into the dish as ground electrode. The MEA can be connected to the amplifier and data acquisition system (Multi Channel System, Reutlingen, Germany), which includes a heating device to maintain a constant temperature of 37° C. Data can be recorded simultaneously from up to 60 channels (sampling frequency up to 40 kHz) under sterile conditions. The data can be analyzed off-line with a customized toolbox programmed for MATLAB (The Mathworks, Natick, Mass., USA) to detect field potentials.

Example 2

Extracellular Recording of Field Action Potentials (fAP) of Purified Cardiomyocytes In accordance with the methods described in international applications WO2004/113515 and WO2005/005621 incorporating the disclosure of international applications WO02/

051987 and WO99/01552 EGFP-positive atrial and pacemaker-like cardiac cells can be derived from stem cells which have been genetically engineered with a recombinant GFP gene under the control of selective promoters and carrying the puromycin resistance gene; see, e.g., Kolossov et al., FASEB J. 19 (2005), 577-579. After mass culture as, for example, described in international application WO2005/005621, comprising ten 12×12 cm² culture dishes with approximately 4000 EBs/20 ml and medium exchange (IMDM+20% FCS) every second or third day, respectively, through cell screens with nylon membrane, and selection with puromycin for 9-14 days the resultant EBs are transferred into 50 ml tubes and washed twice with PBS. After treatment with trypsin for 10 minutes with twice pipetting with a 1 ml pipette almost perfect dissociation is achieved, approximately $1.5 \times 10^6$ green cells. The dissociated cells are plated on fibronectin-coated plates and medium is exchanged the next day, i.e. on day 15 after culture, thereby removing most of the cell debris and dead cells.

For plating on MEAs the resultant cardiac cells are washed twice with ice cold PBS with $Ca^{2+}/Mg^{2+}$. Thereafter, the cells are incubated on ice for 30 minutes and washed twice with PBS w/o $Ca^{2+}/Mg^{2+}$. Trypsinization is followed for 5 minutes at 37° C. resulting in approximately $8 \times 10^5$ EGFP-positive cells.

The cells are then plated on fibronectin-coated MEA ($3.3 \times 10^5$ EGFP-positive cardiac cells). To this end, MEAs were plasma cleaned and coated with bovine placental fibronectin for approximately 4 hours at 4° C. Residual fibronectin was sucked off and MEAs were dried on clean bench.

Selected, dissociated and replated atrial and pacemaker cells on fibronectin-coated MEAs can be used for acute as well as longterm analysis on a single level or in total by means of recording from the substrate integrated microelectrodes.

In another experiment ventricular cardiomyocytes were generated from EBs derived from mouse embryonic stem cell line D3 (see Doetschman et al., 1985, 1988), supra, which were transfected with a construct comprising the puromycin resistance- and EGFP-expression cassettes under the control of the murine MLC2v promoter (RPLC2v, gene bank Accession No. AF302688) based on the parental pIRES2-EGFP vector (Clontech).

For the setup of mass culture, these genetically modified ES cells are trypsinized, seeded with $2 \times 10^5$ cells/ml in KO-DMEM+15% SR and cultured in suspension on a shaker. On day 4 the resultant EBs are plated with 500 to 2000 EBs per 15 cm cell culture dish with gelatin-coating (20 dishes).

At day 11, 0.4 µl/ml puromycin is added to the cell culture dishes and on the following day the medium is exchanged and another 1 µl/ml puromycin is added. At day 14 the cells are combined and trypsinized. From these cells $1.1 \times 10^5$ EGFP-positive cells were plated on one fibronectin 6 cm dish with puromycin (0.4 µl/ml) resulting in approximately 27 ventricular cardiomyocytes per EB. At day 17 ventricular cells are trypsinized and plated on MEAs yielding $6 \times 10^4$ purified cells corresponding to approximately 15 ventricular cardiomyocytes/EB.

MEA recordings may be performed from the monolayer of purified ventricular cardiomyocytes 1, 2 and 7 days after plating on MEA. In accordance with the present invention it could be shown that the recordings from selected electrodes reflect typical long field action potential durations (fAPD), as expected for ventricular cardiomyocytes.

As described above, purified ES cell-derived cardiomyocytes may also be seeded in lower density ($5 \times 10^4$ cells per MEA) and single cell analysis may be performed on these autonomously beating cells, for example by transmission light and fluorescence picturing and recordings from single cells on MEA electrodes.

Taken together it could be demonstrated in accordance with the present invention that ES cell-derived in vitro differentiated tissue and cells in combination with microelectrode array technique can be used for quantitative and qualitative toxicity testing and drug evaluation. As described in the examples, preferably either embryoid bodies may be used or selected, dissociated and replated differentiated cells derived thereof, depending on the parameters to be tested. In summary, a non-invasive, in vitro functional cell and tissue assay system is provided.

It will be recognized that the compositions and procedures provided in the description can be effectively modified by those skilled in the art without departing from the spirit of the invention embodied in the claims that follow.

The invention claimed is:
1. An in vitro method for screening a test substance for an effect on a cardiomyocyte, comprising:
    (a) providing cardiomyocytes having been obtained by differentiating mouse or human pluripotent stem cells;
    wherein the stem cells have been transfected with at least one vector, wherein the at least one vector comprises a first nucleotide sequence encoding a selectable marker and the at least one vector comprises a second nucleotide sequence encoding a reporter gene;
    wherein the transfected stem cells comprise the first nucleotide sequence operably linked to at least one cardiac cell-specific regulatory sequence and comprise the second nucleotide sequence operably linked to a cardiac cell-specific regulatory sequence, and
    wherein the cardiomyocytes have been selected based on expression of the selectable marker;
    (b) contacting cardiomyocytes of step (a) with a test substance, wherein the cardiomyocytes have been placed on an electrode array;
    (c) measuring the electrical activity of the contacted cardiomyocytes with the electrode array and analyzing at least one parameter selected from the group consisting of:
        (i) $Na^+$ channel activity,
        (ii) $Ca2^+/K^+$ channel activity,
        (iii) $K^+$ channel activity;
        (iv) amplitude and/or field potential duration,
        (v) chronotropy,
        (vi) arrhythmia,
        (vii) pH-value,
        (viii) oxygen partial pressure,
        (ix) beating arrest,
        (x) contractility,
        (xi) analysis of AV-dissociation contractility,
        (xii) conductivity and/or impedance,
        (xiii) nitrous oxide-effects, or
        (ix) morphological changes;
    (d) selecting a test substance that has an effect on at least one parameter in step (c) as compared to cardiomyocytes which were not contacted with a test substance and wherein a change in at least one parameter measured in step (c) indicates that the test substance has an effect on a cardiomyocyte.
2. The assay method of claim 1, wherein said pluripotent stem cells are embryonic stem (ES) cells.

3. The method of claim 1, wherein said electrode array is a multi- or microelectrode array (MEA).

4. The method of claim 3, wherein the electrode array is coated with fibronectin.

5. The method of claim 1, wherein at least one of the parameters analyzed is selected from the group consisting of: beating frequency, mean contractility, maximum contraction and mean area of contraction is analyzed.

6. The method of claim 1, wherein test substance is one of a collection of test substances.

7. The method of claim 6, wherein said collection of test substances comprises about $10^3$ to about $10^5$ substances.

8. The method of claim 1, wherein three or more measurements are taken.

9. The method of claim 1, further comprising isolating the measured cardiomyocytes.

10. The method of claim 8, wherein said measurements are taken at different positions within the array.

11. The method of claim 1, wherein said selection step positively screens a test substance.

12. The method of claim 1, wherein said selection step screens out a test substance.

* * * * *